US006662162B2

United States Patent
Casper

(10) Patent No.: US 6,662,162 B2
(45) Date of Patent: Dec. 9, 2003

(54) METHOD OF RATING MOTOR DYSFUNCTION BY ASSESSING SPEECH PROSODY

(76) Inventor: Maureen Casper, 48 Tyler Cir., Rye, NY (US) 10580

( * ) Notice: Subject to any disclaimer, the term of this patent is extended or adjusted under 35 U.S.C. 154(b) by 49 days.

(21) Appl. No.: 09/942,097

(22) Filed: Aug. 28, 2001

(65) Prior Publication Data

US 2002/0062067 A1 May 23, 2002

Related U.S. Application Data

(60) Provisional application No. 60/228,386, filed on Aug. 28, 2000.

(51) Int. Cl.[7] .............................................. G10L 21/00
(52) U.S. Cl. ..................................................... 704/271
(58) Field of Search ................. 704/271, 270, 704/275, 236, 206; 434/185

(56) References Cited

U.S. PATENT DOCUMENTS 4,543,957 A * 10/1985 Friedman et al. ............ 128/630
5,864,812 A * 1/1999 Kamai et al. ................ 704/268

OTHER PUBLICATIONS

Beckman & Cohen, "Modeling the articulatory dynamics of two levels of stress contrast", presented at the conference of the Acoustical Society of America, Nov. 27–Dec. 1, 1995 in St. Louis, MO.
Beckman & Edwards, In P. Keating (ed.), Papers in Laboratory Phonology III, pp. 7–33, Cambridge, U.K: Cambridge University Press.
Bell–Bertl et al., In Proceedings of the 12th International Congress of Phonetic Sciences, pp. 262–265, Aix–en Provence.
Bell Bertl et al., In Proceedings of the 13th International Congress of Phonetic Sciences, pp. 162–165, Stockholm.
Darley et al., Journal of Speech and Hearing Research, 1969, 12:246–269.
Edwards et al., J. Acoust. Sci. Am., 1991, 89(1):369–382.
Harris, Language and Speech, 1978, 21(4):354–361.
Jong et al., Language and Speech, 1993, 36(2,3):197–212.
Kent et al., Journal of Speech, Language, and Hearing Research, 2000, 43:1275–1289.
Kent et al., Journal of Speech and Hearing Research, 1979, 22:627–648.
Lindblom, The Journal of the Acoustical Society of America, 1963, 35(11):1773–1781.
Ziegler et al., Journal of Speech and Hearing Research, 1993, 36:683–693.

* cited by examiner

Primary Examiner—Susan McFadden
(74) Attorney, Agent, or Firm—Darby & Darby

(57) ABSTRACT

The present method provides an acoustic signature with correlation to neurological degeneration for the speech disturbances. Acoustic measures of speech disturbance can be compared to or rated against neurological measures or indicators such as magnetic resonance imaging to diagnose a neurological condition or to rate the severity or progression of a condition.

16 Claims, 15 Drawing Sheets

METHOD OF RATING MOTOR DYSFUNCTION BY ASSESSING SPEECH PROSODY

This application claims priority of U.S. provisional application Ser. No. 60/228,386, filed Aug. 28, 2000.

FIELD OF THE INVENTION

This invention relates to an acoustic based method of identifying and rating motor speech deterioration and the underlying pathologies of the deterioration.

BACKGROUND OF THE INVENTION

Ataxia is a profound loss of muscular coordination which characterizes cerebellar-based pathology (Diener & Dichgans, 1992). A loss of coordination in ataxia may take the form of the loss of balance, the inability to walk heel to toe, nystagmus, difficulty alternating sequences of movements, dysarthria (Diener, & Dichgans, 1992), dysmetria and hypermetria (Hallet, Shahani, & Young, 1975 a, b).

Kinematic/electromyographic (EMG) studies of speech have investigated both normal muscle activation patterns (Harris, 1978; Tuller, Harris, & Kelso, 1981) and muscle patterns in ataxic dysarthric speakers (Ackermann, Hertrich, Daum, Scharf, & Spieker, 1997; (Ackermannn, Hertrich, & Scharf, 1995). Several investigations have also focused on the possible similarities or differences between limb movements and speech movements in ataxia. (Gentil, Devanne, Maton, & Brice, 1992; Salisachs, 1979; Akermann et al., 1995; Ostry, Keller, & Parush, 1983).

Early descriptions of dysarthria (Darley, Aronson & Brown, 1969a., b) were based solely on the perceptual judgments of several speech and voice characteristics. The 10 speech and voice characteristics of ataxic dysarthria (Darley et al., 1969a), typified by poor coordination of the articulators, were grouped into three clusters: 1. articulatory inaccuracy (imprecise consonants, irregular articulatory breakdown, and distorted vowels); 2. prosodic excess (excess and equal stress, prolonged phonemes, prolonged intervals, and slow rate); and 3. phonatory-prosodic insufficiency (monopitch, monoloudness, and harsh voice). However, perceptual descriptions are misleading and the distinctive patterns once claimed, do not hold for comparisons of neurological syndromes (Ziegler) or for those patterns found in ataxic speakers.

Subsequent studies attempted to supplement the perceptual description of ataxic dysarthria with acoustic analyses (see e.g., Kent, Netsell, & Abbs, 1979), however, they did not describe the prosodic descriptors in acoustic terms nor correlated their analyses with neurological pathological conditions.

Acoustic descriptions of ataxic speech were used to measure duration and first and second formant onset/offset frequencies. In studies using ataxic subjects, Kent et al. used acoustic measurement to describe ataxic speech and concluded that that formant frequencies were normal in ataxic subjects while duration measures were not. However the speaker tasks were many and did not capture the disturbance of syllables in several contexts. Thus whether this finding held for words within a phrase, or for syllables or words within sentences was not known. Further, although the acoustic analysis of dysarthria caused by cerebellar damage found a disproportionate lengthening of the segment to be a fundamental property of ataxic dysarthria (Kent et al., 1979), it was not known whether this was a property specific to ataxic dysarthria, or was present in all or some other dysarthrias. Examining narrow band spectrograms of sentences led Kent et al. to suggest a syllable-level planning with a falling f0 on each successive syllable. The lengthening of segments and syllables led the investigators to posit a disordered prosody for cerebellar subjects.

Prosody in normal speech production has included descriptions of F0, formant frequencies and syllable duration. These acoustic descriptions have not described the dissociation between time (duration) and space (oral pharyngeal space) inferred from formant frequency values F1 and F2. This dissociation is important because it allows for description of pathological utterances that are long and reduced in movements (slurred speech) and the slowing down of normal speech that occurs at the end of utterances. Previously models of speech predicted that all lengthened syllables would have more extreme movements.

A critical issue in the study of speech motor control is the identification of the mechanisms that generate the temporal flow of serially ordered articulatory events. Early investigations were motivated by Lashley's (1951) model that predicted a monotonic relationship between vowel duration and formant frequency. Lindblom (1963), for instance, claimed that articulatory "undershoot" is the basis for any reduction in vowel duration from normal values.

Subsequent studies did not find that duration and formant frequency were monotonically linked. Harris (1978) found that, contrary to the predictions of Lindblom's model, when either rate or stress was manipulated, syllable duration and vowel formant frequency varied independently in a non-monotonic relation. In addition, EMG studies showed reduced orbicularis oris and genioglossus activity for syllables of reduced stress (Tuller et al., 1981; Harris, 1971, 1978). The conclusions drawn from these physiological and acoustic data of normal speakers was that any change in rate or stress may result in independent variations of syllable duration and formant values.

The components of prosody have been defined as the acoustic features of f0, segment duration, amplitude and segmental quality. Variations in the values of these features signal, among other things, constituent boundaries and syllable prominence. The kinematic data of Cohen et al. (1995) for six different conditions of syllable prominence show a difference in velocity for accented syllables in phrase final vs. non-final position. This kinematic finding speaks to the non-monotonic relation between duration and formant frequencies: all durations are not the same. Sometimes speakers slow down, resulting in reduced vowel space with longer durations; thus there is a dissociation between duration and formant frequency. However, this was not shown in acoustic measures.

It is an object of the invention to provide a reliable quantitative acoustic assessment to describe the speech and voice characteristics of subjects with neuro-motor speech disturbances. It is a further object of the invention to provide a method that can correlate prosodic descriptors in acoustic terms with neurological pathological conditions.

SUMMARY OF THE INVENTION

The present invention provides a method of identifying speech motor dysfunction in a test subject comprising measuring one or more acoustic parameters of one or more prosodic conditions; comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to speech motor dysfunction.

The present invention also provides a method of identifying speech deterioration in a test subject comprising measuring one or more acoustic parameters of one or more prosodic conditions; comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to speech deterioration.

The present invention further provides a method of diagnosing speech motor dysfunction in a test subject comprising measuring one or more acoustic parameters of one or more prosodic conditions; comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to speech motor dysfunction.

In another embodiment, the present invention provides a method of rating the severity of speech motor dysfunction in a test subject comprising measuring one or more acoustic parameters of one or more prosodic conditions; comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to a rating of the severity of the speech motor dysfunction.

The acoustic parameters comprise syllable duration, f0, F1 and F2. The prosodic conditions comprise (1) phrase-final accented (+pf+a), (2) non-phrase-final accented (−pf+a), (3) non-phrase-final unaccented (−pf−a), (4) nuclear accented (+n+a), (5) post nuclear unaccented (−n−a) and (6) reduced vowel (red).

According to the methods of the invention, the contrast values are compared using the equation (Test: (+pf+a)−(−pf+a)−Control (+pf+a)−(−pf−a)2+(Test: (−pf+a)−(−pf−a)−Control: (−pf+a)−(−pf+a)2+(Test: (+n+a)−(−n−a)−Control (+n+a)−(−n−a)2+(Test: (−n−a)−(red)−Control: (−n−a)−(red)2 wherein

| | |
|---|---|
| +pf+a = | accented syllables in phrase final; |
| −pf+a = | accented syllables in non-phrase final; |
| −pf−a = | unaccented syllables in non phrase final; |
| +n+ = | nuclear accented; |
| −n−a = | post-nuclear unaccented syllables; and |
| red = | reduced CVC syllables. |
| Test = | subject |
| Control = | control. |

The present invention provides a means of identifying abnormal speech and voice patterns based on a comparison to a normal model of speech and voice patterns. The present invention further provides an accurate and sensitive acoustically-based method of identifying system of deterioration of motor function. The method may be useful for the screening and diagnosis of cerebellar-based pathological conditions or other conditions in which both speech/motor function is deteriorated or impaired.

BRIEF DESCRIPTION OF THE FIGURES

FIG. 10 shows mean ft at mid-point in Hz for each of the four prosodic contrasts for cerebellar ataxic speakers and normal speakers. The difference in means within each group is represented as significant by *(p<0.05) and **(p<0.01). The mean difference between groups for each of the four contrasts is marked for significance on the x axis:+n+a/–n–a.

DETAILED DESCRIPTION OF THE INVENTION

Figure 1:
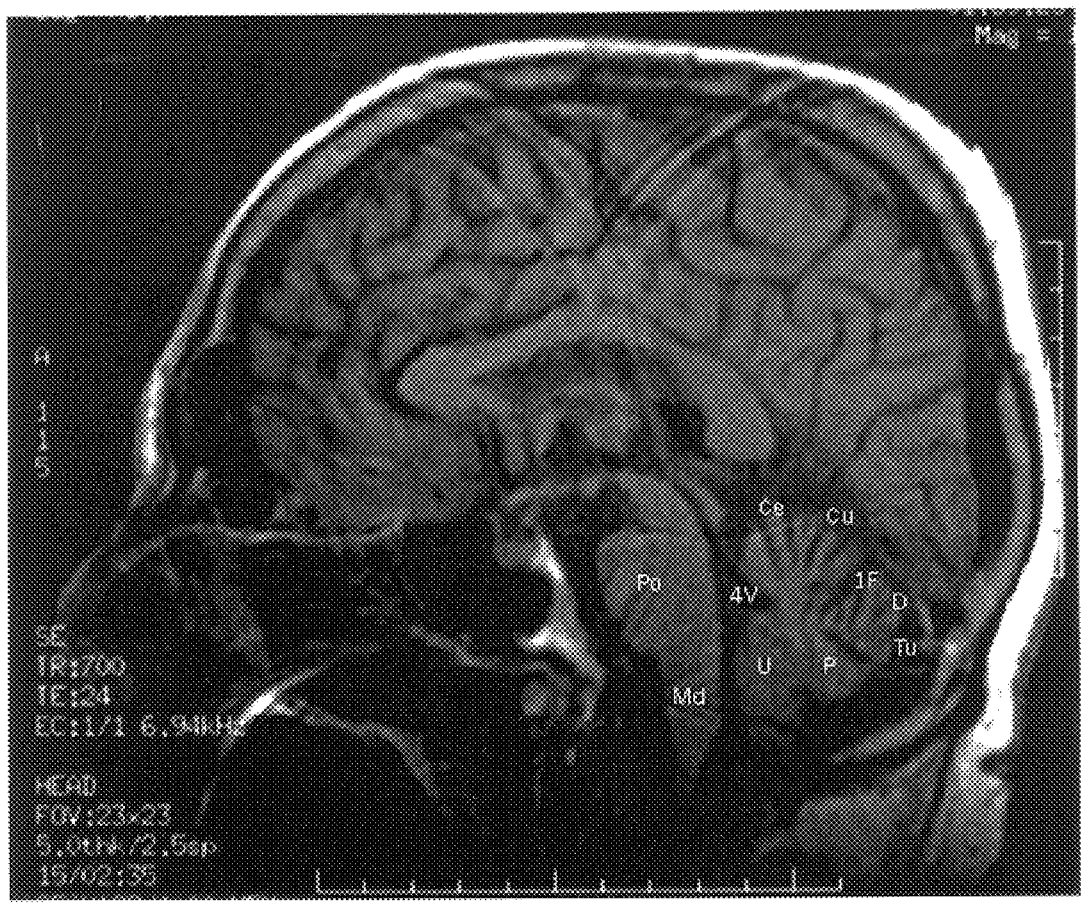
FIG. 1 shows an MRI of the midsagittal section of the left side of the brain in ataxic male subject 1. The most apparent finding is atrophy of the cerebellar vermis involving the primary degeneration of the central lobule (Ce),cumen (Cu), declive (D) and tuber (Tu). In addition there is a widening of the primary fissure (1F). The pyramid and uvula remain relatively intact. Other structures labeled include the pons (Po), medulla (Md) and the $4^{th}$ ventricle (4 V). This subject was given a radiological rating of atrophy of 2.0
Figure 2:
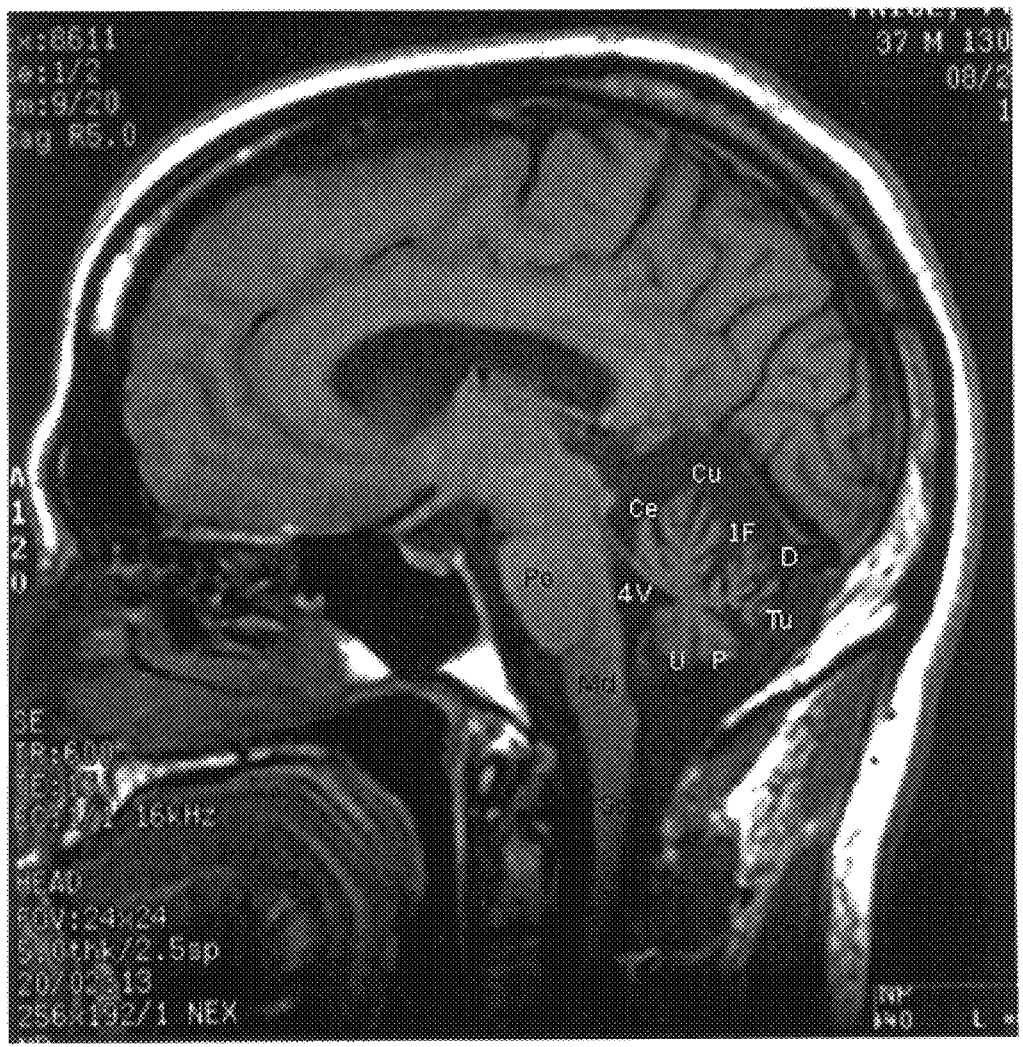
FIG. 2 shows an MRI of the midsagittal section of the left side of the brain in ataxic male subject 2. The most apparent finding is atrophy of the cerebellar vermis including primary degeneration of the central lobule (Ce), cumen (Cu), declive (D) and tuber (Tu). Other structures labeled include the pons (Po), medulla (Md), spinal chord (Sc) and the pyramid (P) and the uvula (U) of the vermis. This subject was given a radiological rating of atrophy of 3.0.
Figure 3:
FIG. 3 shows an MRI of the midsagittal section of the left side of the brain in ataxic male subject 3. The most apparent finding is atrophy of the cerebellular vermis including primary degeneration of the central lobule (Ce), cumen (Cu), declive (D) and tuber (Tu). In addition, there is a widening of the primary fissure (1F). The pyramid (P) and uvula (U) remain relatively intact. Other structures labeled include the pons (Po), medulla (Md), $4^{th}$ ventricle (4 V), corpus callosum: (genu CCG) body (CCB) and splenium (CCS), thalmus (Th) and hypothalmus (Hy Th). This subject was given a radiological rating of atrophy of 2.5.
Figure 4:
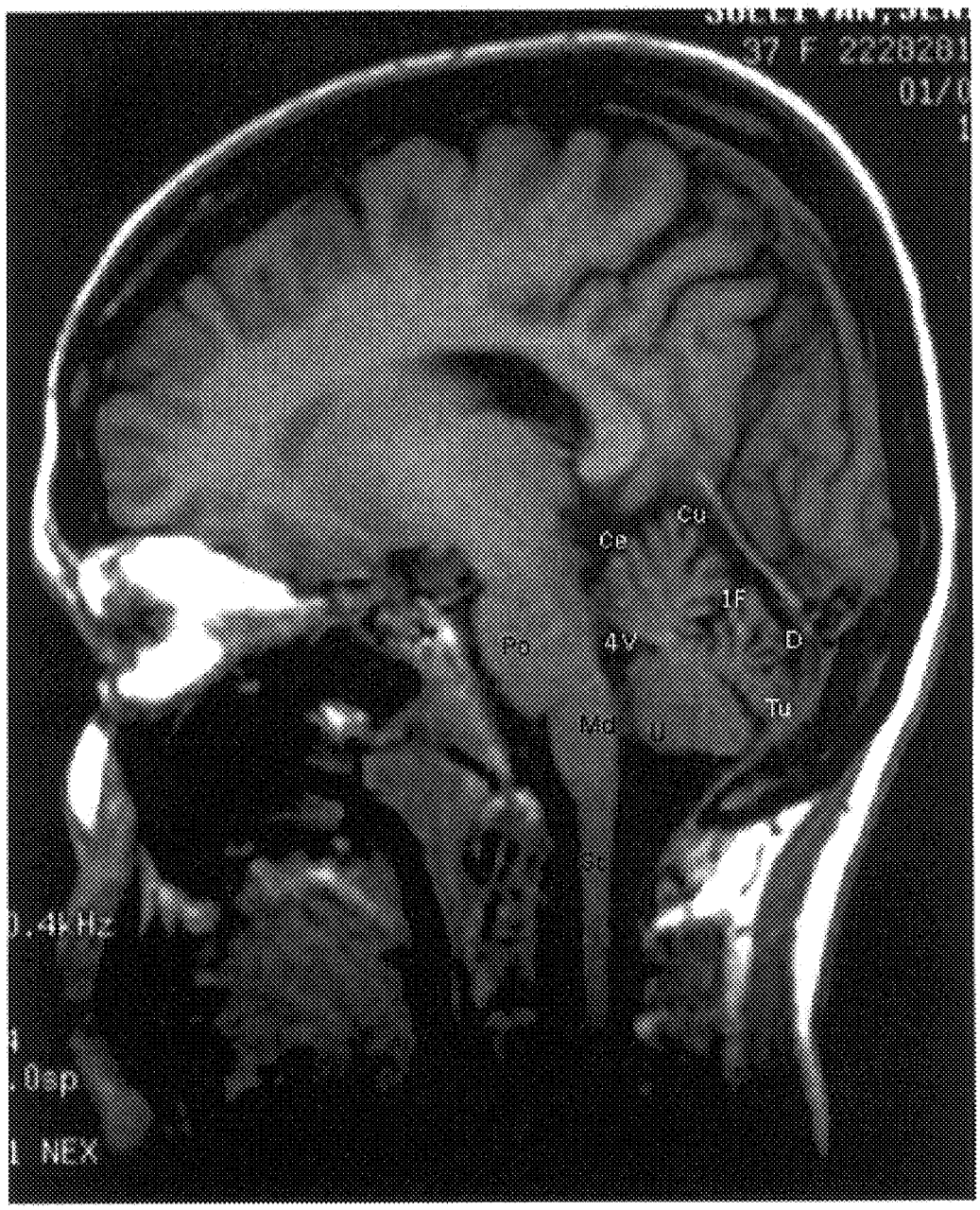
FIG. 4 shows an MRI of the midsagittal section of the left side of the brain in female ataxic, of the Friedreich's sub-type, subject 4. The most salient feature is atrophy of the cervical cord. The cerebellar vermis shows atrophy primarily in the central lobule (Ce), cumen (Cu), declive (D) and tuber (Tu). Other structures labeled include the primary fissure (1F), the pons (Po), medulla (Md), and spinal cord (Sc). This subject was given a radiological rating of atrophy of 2.0.
Figure 5:
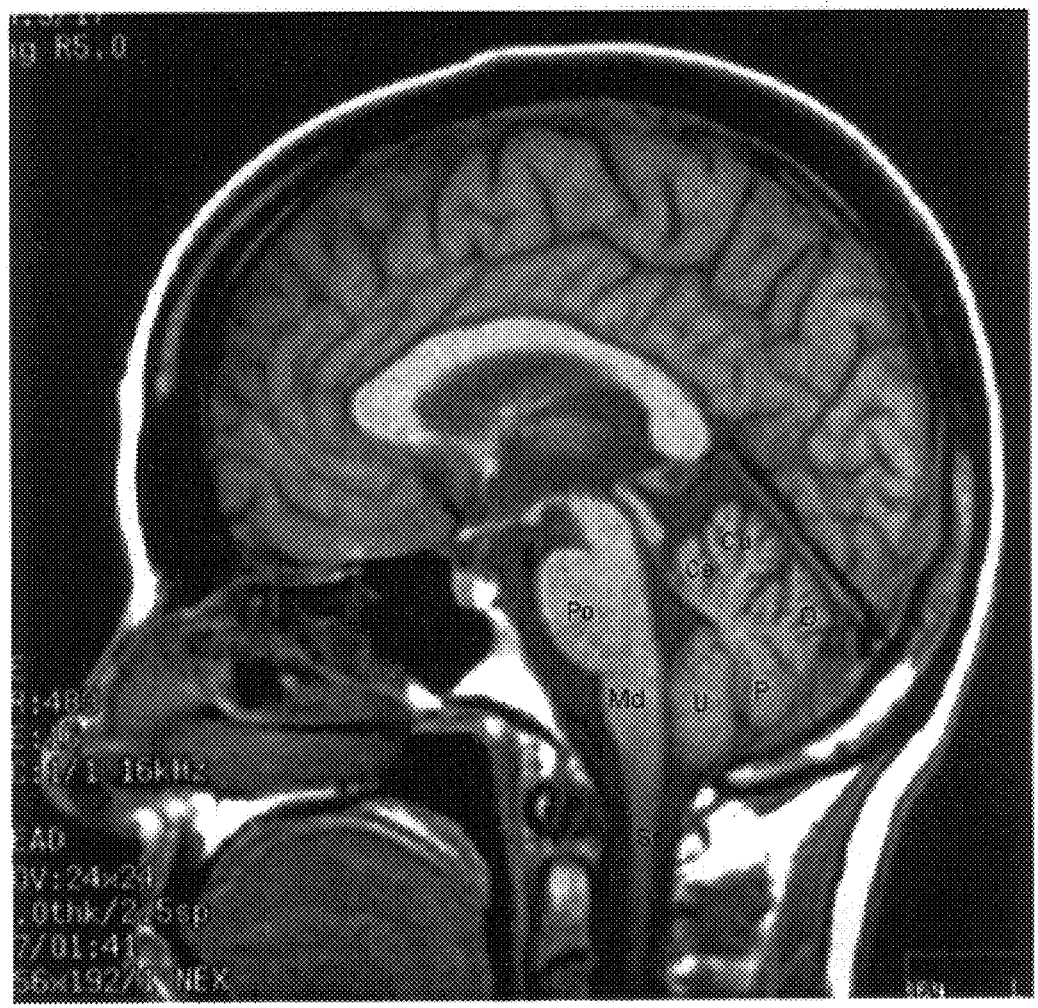
FIG. 5 shows an MRI of the midsagittal section of the left side of the brain in ataxic subject (Freidreich's sub-type) 5. The most apparent finding is atrophy of the spinal cord. Atrophy of the cerebellar vermis is recognized in the degeneration of the central lobule (Ce), cumen (Cu), declive (D) and tuber (Tu). In addition, there is a widening of the primary fissure (1F). The pyramid (P) and uvula (U) remain relatively intact. Other structures labeled include the pons (Po), medulla (Md), and spinal cord (Sc). This subject was given a radiological rating of atrophy of 2.0.
Figure 6:
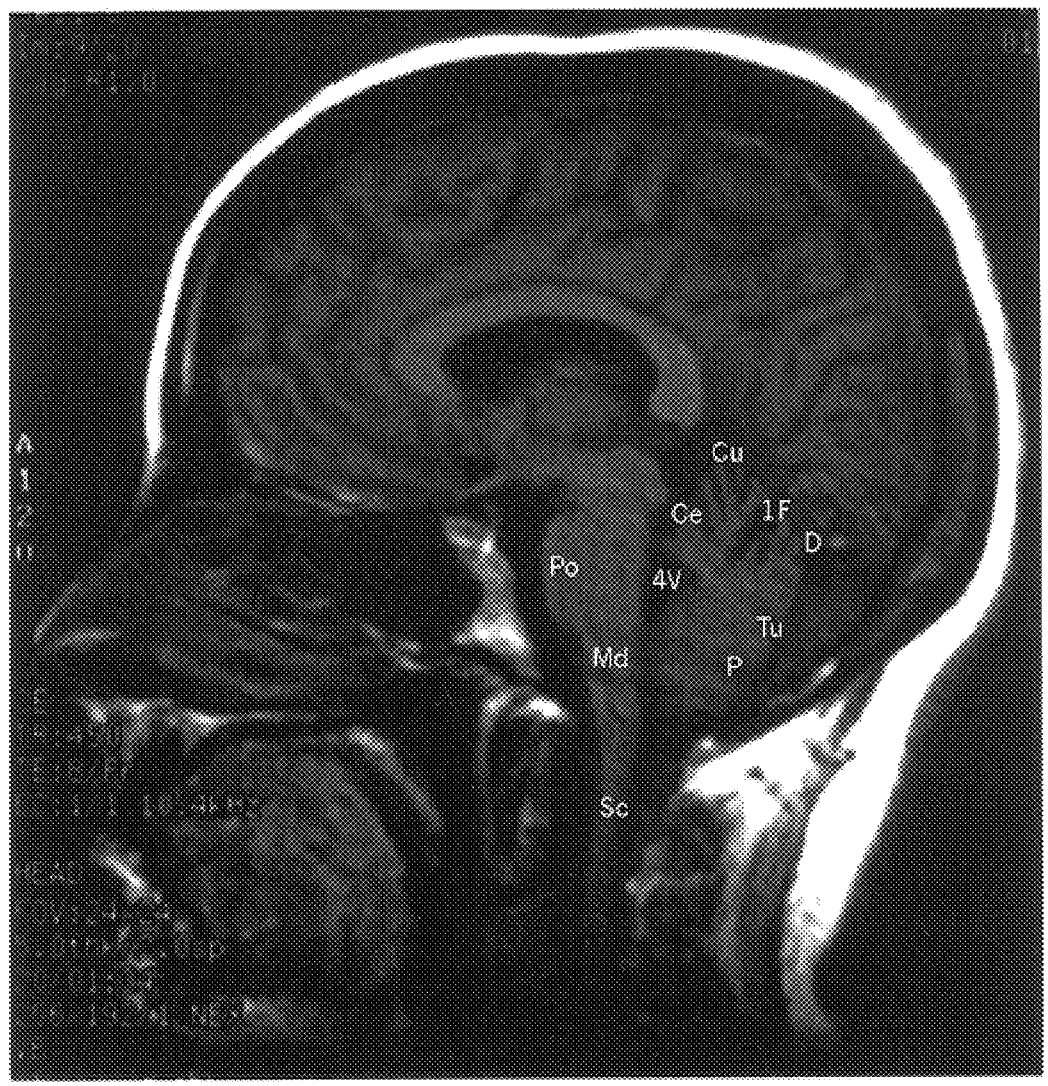
FIG. 6 shows an MRI of the sagittal section of the left side of the brain in ataxic subject 6. The most apparent finding is atrophy of the spinal cord (Sc). Atrophy of the vermis is limited to the central lobule (Ce), cumen (Cu), declive (D) and tuber (Tu). The tuber (Tu) and pyramid (P) remain relatively intact. Other structures labeled include the primary fissure (1F), $4^{th}$ ventricle (4 V), pons (Po) and medulla oblongata (Md). This subject was given a radiological rating of atrophy of 1.5.
Figure 7:
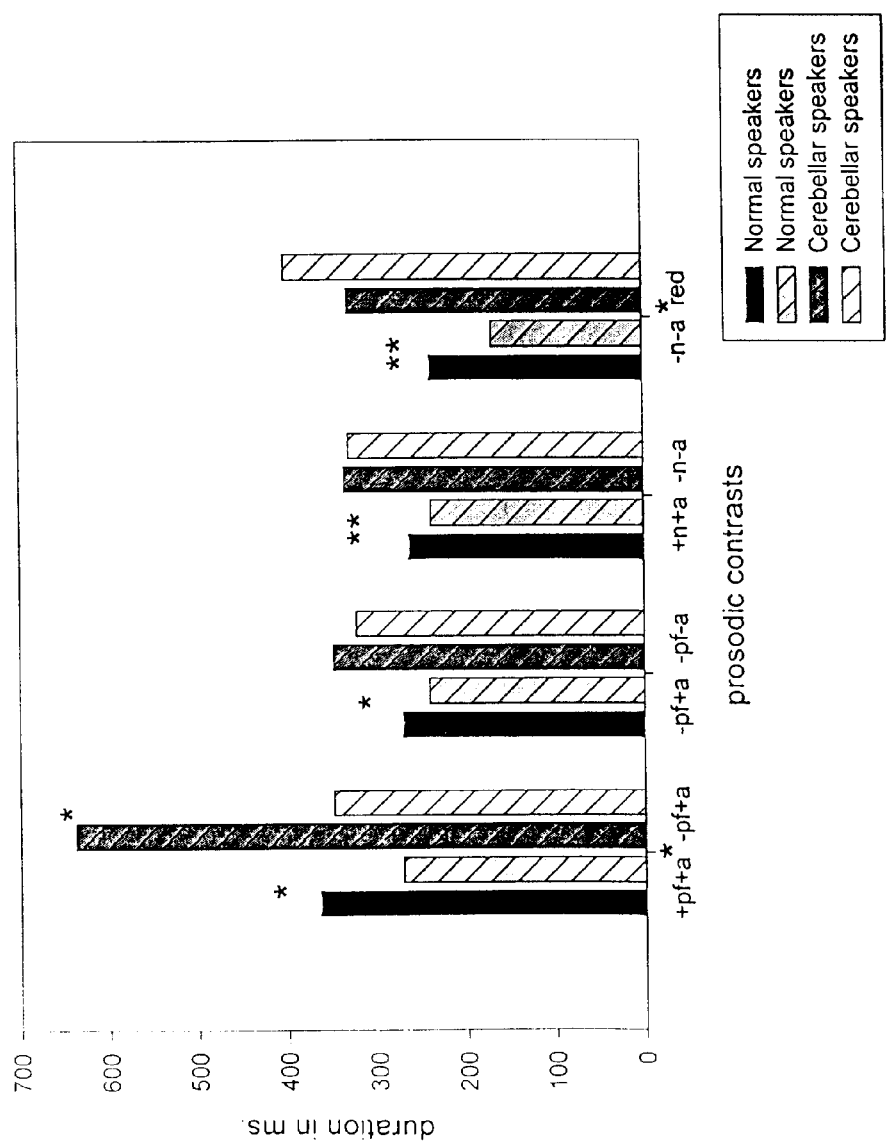
FIG. 7 shows mean syllable durations in milliseconds (ms) for each of the four prosodic contrasts for cerebellar ataxic speakers and normal speakers. The difference in means within each group is represented as significant by *($p<0.05$) and **($p<0.01$). The mean difference between groups for each of four contrasts is also marked for significance on the x-axis: +pf+a/−pf+a and −n−a/red.

The present invention provides a model for identifying a normal speech and voice pattern in a subject and using this model as the basis of a method to identify deterioration of normal speech and voice patterns in a subject suffering from a neurological condition. The acoustic model of speech prosody provides a normal model that may be used to assess speech motor dysfunction. The model is based on a comparative design wherein one prosodic condition is measured against another prosodic condition within the same acoustic measure to obtain a comparative value. Normal speakers consistently show significant differences in specific directions for the four prosodic contrasts investigated. It is these differences and directions that represent a normal speaker's motor adaptation to stress. A loss of function is represented in a speaker's inability to produce the same differences and the direction of those differences. In cerebellar ataxic speakers two differences were recognized, but the direction of these differences were opposite from the normal control.

Definitions

"Prosody" is the description of rhythm and tonal patterns of speech. The description is provided by acoustic parameters, variations in which signal constituent boundaries and prominence: F0, duration, amplitude and segment quality or reduction.

"Speech motor dysfunction" or "Dysarthria" is a disorder to articulation and voice caused by impairment of parts of the nervous system that control the muscles of voice and articulation.

"Formant" is a peak of resonance in the vocal tract; formants are displayed in a wideband spectrogram as broad bands of energy.

"Fundamental Frequency" (f0) is the lowest frequency component of a complex periodic wave or the repetition rate of a complex periodic wave.

"Cerebellum" is a main division of the brain situated behind the cerebrum and above the pons; its function is to coordinate movement including speech movement.

"Prosodic Conditions" are the different syllable contexts within a phrase, sentence or multi-syllabic word that influence the acoustic variables of fundamental frequency, formant frequencies and syllable duration. These acoustic parameters relate to speech rhythm and intonation.

"F1" and "F2" are acoustic measures that are correlated to the dimensions of the oral and pharyngeal cavities and the tongue, jaw and lip position in vowel articulation.

"Syllable Duration" is the amount of time for speaking the target syllable in ms, timed from the release of the lips represented by a burst of energy on the spectrogram to the release of the lips at the end of the target syllable.

"Prosodic Contrasts" are used to define normal patterns of speech. A prosodic contrast consists of two conditions where the difference between the means of two prosodic conditions results in a value for description, identification and comparison between groups. "Subject" is the person being tested.

"Neurological condition" means speech motor disorders or dysarthrias, including cerebellar disorders, bulbar palsy, pseudobulbar palsy, parkinsonism, dystonia, chorea, multiple sclerosis and amyotrophic lateral sclerosis, sub-types of cerebellar degeneration (see, e.g., Plaitakias, Katoh & Huang 1992) and conditions where speech motor function is affected by drugs (pharmaceutical/therapeutic administration) or alcohol.

The method of the present invention shows that limb movement and speech movement may be correlated. The measures obtained by the method supports movement data (kinematics) which describes different patterns of movement in lengthened syllables: some lengthened syllables have reduced movement: i.e. phrase final syllables in normal speakers; reduced syllables regardless of position in pathological speakers.

The method comprises measuring one or more acoustic parameters of one or more prosodic conditions; comparing each acoustic parameter between pairs of prosodic conditions to obtain a contrast value; and comparing the contrast values for each acoustic parameter, wherein the comparison identifies a normal speech pattern.

The acoustic model of speech prosody described herein may be used to assess speech motor dysfunction in those individuals with "speech motor disorders or the dysarthrias". Thus the method of the invention may be used to identify or diagnose any condition in which speech/motor function is impaired (such as with short term or long term alcohol or drug use) or deteriorated (due to disease).

The present methods provide an acoustic signature with correlation to neurological degeneration for the speech disturbance recognized in cerebellar degeneration. Acoustic measures of speech disturbance in ataxic speakers can be compared to or rated against neurological measures or indicators such as magnetic resonance imaging to diagnose a neurological condition or to rate the severity or progression of a condition.

Thus the measurements of speech as described herein also may identify the underlying etiology of the deterioration of limb movement and speech movement. The method of measuring speech and voice of the invention is both sensitive and quantitative and allows for identification of motor dysfunction regardless of the cause, e.g., disease, toxicity or trauma. The methods also describe the voice and speech patterns for neurological disorders. The methods also rate the severity of such disorders and may provide a differential diagnosis of disorders within a syndrome and between syndromes. For example, based on the methods, a database may be formed which contains the patterns identified both for normal and any number of speech motor dysfunctions, providing standards for each condition. Values obtained by the methods described herein can be compared to the standard values and a rating of severity or differential diagnosis may be generated. Those patterns recognized may also be used to guide therapeutic intervention, both pharmaceutical and behavioral.

Specifically, a value termed the "D" score is obtained. The D score is a quantitative measurement of the difference in patterns measured between subjects. The D score is obtained using the equation (Test: (+pf+a)−(−pf+a)−Control (+pf+a)−(−pf−a)2+(Test: (−pf+a)−(−pf−a)−Control: (−pf+a)−(−pf+a)2+(Test: (+n+a)−(−n−a)−Control (+n+a)−(−n−a)2+(Test: (−n−a)−(red)−Control: (−n−a)−(red)2 wherein

| | |
|---|---|
| +pf+a = | accented syllables in phrase final; |
| −pf+a = | accented syllables in non-phrase final; |
| −pf−a = | unaccented syllables in non phrase final; |
| +n+ = | nuclear accented; |
| −n−a = | post-nuclear unaccented syllables; and |
| red = | reduced CVC syllables. |
| Test = | subject |
| Control = | control. |

The diagnostic value of the D score is shown in different patterns revealed in Friedrich's ataxic and cerebellar ataxic speakers. The detection of these patterns support this measure as a sensitive index of pathology, one that can identify differences in a syndrome (cerebellar pathology) that perceptually may appear to be similar to listeners. This measure may also be useful in differentiating across syndromes.

The prosodic contrasts that form the basis of the invention yield systematic and significant variation in acoustic parameters for normal speakers; these parameters may vary between normal and cerebellar or may not be found in cerebellar speakers. Based on the sensitive behavioral analyses described below, it was found that cerebellar speakers adapted differently to the demands of stress placement than did normal subjects.

The production of prosodically normal speech requires rapid adaptability within an utterance. The acoustic measures used to quantify this normal adaptation (syllable duration, f0, 1 and F2) clearly showed that cerebellar speakers, although intelligible, demonstrated a deterioration in speech that was acoustically measurable. Cerebellar speech was markedly slow and failed in the rapid adaptation to reduce frequency and shorten length for syllables that are produced with less prominence in the normal utterance. For example for Formants: F1 and F2 resonant frequencies of the oral-pharyngeal cavity showed differences in normal speakers and cerebellar speakers. These findings allow a means of inferring abnormal movement patterns of speech motor dysfunction.

The studies further showed that differences were observed between measures within the group of normal speakers. In normal prosody, a flexible response occurs, represented in systematically varying degrees of prominence. The acoustic measurement of this prominence, revealed a systematic variability in these parameters in the normal speakers. This systematic variability was recognized statistically within the pair-wise comparisons of prosodic contrasts produced by the normal speakers. Thus the methods of the invention may be useful for setting standards for normal speech patterns and identification of voice patterns.

The methods described herein are based on the study described below wherein the spatial-temporal properties of syllable production in ataxic and normal speakers were examined in twelve speakers (six ataxics and six normals). The speaking task was designed to elicit six different prosodic conditions and four contrastive prosodic events. The normal speakers showed statistically significant differences for all four prosodic contrasts. The cerebellar speakers showed a different pattern of lengthening and syllable reduction from the normal speakers. An estimate of speech deterioration as determined by individual differences between cerebellar and normal subjects' acoustic values of the four prosodic contrasts was then used in correlation analyses with MRI ratings. Moderate correlations between speech deterioration and cerebellar atrophy were found in the measures of syllable duration and f0. A strong negative correlation was found for F1. The normal model described by the prosodic contrasts provides a sensitive index of cerebellar pathology with quantitative acoustic analyses.

EXAMPLE

The purpose of the study described below was to investigate acoustically the effects of cerebellar pathology on certain aspects of speech prosody. Cerebellar pathology was identified by neurological diagnoses and magnetic resonance imaging (MRI). The study compared syllable duration, formant frequency (F1 and F2), and fundamental frequency (f0) of syllables under various conditions of accent and phrase position in normals subjects and subjects with cerebellar disorder.

"Spectrogram" is a display of the components (harmonics and formants) of sounds as they vary in frequency and intensity over time. Frequency is shown on the abscissa and intensity as relative darkness of the image.

"F statistic" is a statistic used to test for a significant difference among several means in an ANOVA or analysis of variance.

"Df" are degrees of freedom of a single sample.

Materials and Methods

Subjects

Two groups of subjects were selected for the study: six normal subjects and six cerebellar subjects. The cerebellar subjects were diagnosed by a neurologist as having cerebellar degeneration with accompanying ataxia of both limb and speech: three subjects with Friedreich's ataxia (4, 6 and 5), one subject with olivo-ponto cerebellar degeneration (3), one subject with pure-recessive cerebellar degeneration (1), and one subject with cerebellar degeneration of unknown etiology (2).

The cerebellar subjects were also classified by MRI as having cerebellar degeneration. All cerebellar ataxic subjects received Magnetic Resonance Imaging (MRI) within one month of the recording of the acoustical samples for analyses of the sites of atrophy within the nervous system. Three views of anatomical MRIs (midsagittal, coronal and transverse) were used to estimate the degree of cerebellar pathology (see FIGS. 1 through 6). Sites of nervous system involvement judged to be affected in relatively different patterns across subjects included the cerebellar vermis and hemispheres, pons, medulla, and spinal cord. The radiological ratings of cerebellar degeneration for the cerebellar subjects are shown in Table 1.

TABLE 1

| Cerebellar Subject | Etiology | Cerebellar Vermis | Cerebellar Hemispheres | Brainstem | Spinal-cord |
|---|---|---|---|---|---|
| 1 | Pure recessive cerebellar degeneration | 2 | 2 | + | − |
| 2 | Unknown | 3 | 3 | − | − |
| 3 | Olivo-ponto-cerebellar atrophy | 3 | 2 | − | − |
| 4 | Friedreich's ataxia | 2 | 2 | − | + |
| 5 | Friedreich's ataxia | 2 | 2 | + | + |
| 6 | Friedreich's ataxia | 2 | 1 | − | + |

Column header: Degree of involvement for selected neural structures

The degree of degeneration was rated by atrophy of the vermis and cerebellar hemispheres on a scale of 0 (no involvement) to 3 (greatest involvement) for each of the cerebellar ataxic subjects. The brainstem and spinal cord were given a rating of (+) for involvement and (−) for no involvement.

The six normal subjects were pair-wise matched to the ataxic speakers by age, sex, dialect, and educational status. All twelve subjects spoke English before the age of twelve years.

Prosodic Conditions

The speech materials used were a series of sentences presented on printed cards. Subjects were instructed to respond to the tester's questions "naturally," by reading the "entire sentence as it appears on the printed card." A list of the elicitation questions and responses is provided in Table 2.

TABLE 2

| Prosodic Condition | Question | Response |
|---|---|---|
| 1. Phrase-final accented (+pf+a) | Who was opposing the question? | Pop, opposing the question strongly, refused to answer it. |
| 2. Non-phrase-final accented (−pf+a) | Who was posing the question? | Papa, posing the question loudly, refused to answer it. |
| 3. Non-phrase-final unaccented (−pf−a) | Who posed the question? | Papa posed the question loudly, and then refused to answer it. |
| 4. Nuclear-accented (+n+a) | Did her mama pose a problem as far as their getting married? | Her papa posed a problem. |
| 5. Post-nuclear-unaccented (−n−a) and 6. Reduced vowel (red) | Did his papa pose a problem as far as their getting married? | HER pap/pa posed a problem. |

The target syllable CVC "pap" was embedded within each sentence. Each question was designed to elicit a prosodically distinct rendering of the sentences when read. The prosodic conditions of syllable prominence used were (1) phrase-final accented (+pf+a), (2) non-phrase-final accented (−pf+a), (3) non-phrase-final unaccented (−pf−a), (4) nuclear accented (+n+a), (5) post nuclear unaccented (−n−a) and (6) reduced (red). Ten sentences for each of six prosodic conditions were pseudo-randomized for a total of 50 sentences and 60 target syllables. (One sentence contained two samples of the (−n−a and red) conditions.).

Instrumentation and Recording Protocols−+

Speakers were recorded using a Sony digital tape recorder (Model TCD-D7) and a Shure (Model SM10A) head-band unidirectional dynamic microphone. Recordings were made in an acoustically suitable room.

Acoustic Measurements

Acoustic measurements were made using the Kay Elemetrics Computerized Speech Lab (CSL). The signal was captured from a DAT (Digital Audio Tape recorder) recorder to the CSL at a sampling rate of 20,000 Hz. Four measures were taken of the target syllable "pap" under all 6 prosodic conditions:

1) Syllable Duration—Duration measures of "pap" were made by hand from high-resolution gray-scale digital wide-band spectrograms using standard measurement criteria (Hillenbrand et al., 1995; Peterson and Lehiste, 1960). The wide-band spectrograms provided a clear display of the bursts of the initial and final stops which served as boundary markers for all measurements of syllable duration except for those of the reduced vowel condition which did not have the CVC syllable structure of "pap". Durations in this condition were measured from the release burst initiating the second syllable of "pa—pa" to the burst of the initial /_/ of the following word "posed" (CVCV-C).

2) Fundamental frequency (f0)-f0 was calculated at the midpoint by the "pitch extraction" routine of the of Kay Elemetrics Computerized Speech Lab (CSL).

3) First formant frequency (F1) and

4) Second formant frequency (F2).

F1 and F2 were measured at the midpoint of the phonated portion of the target syllable. The F1 and F2 frequencies were used as the basis for inferring vocal tract configuration with regard to mouth opening and degree and location of constriction. Formant frequencies were determined using a combination of wide-band spectrographic analysis, Linear Predictive Coding (LPC) frequency response and Fast Fourier Transformation (FFT) in order to resolve ambiguities caused by the proximity of F1 to F2 in the vowel "a" and the proximity of F1 to f0 (for the female speakers).

A wide-band spectrogram, time-linked to the waveform and displayed below it was used for the preliminary formant frequency measures. The duration of the phonated segment was halved for the mid-point mark. A wide-band power spectrum at the calculated mid-point was generated using Linear Predictive Coding (LPC). In instances when the LPC display did not resolve F1 and F2, a narrowband Fast Fourier Transform (FFT) display was generated. The peak harmonic amplitudes within the bandwidths of F1 and F2 were taken as a discrete measure of the frequencies of the formants. In order to assure consistency of measurement, this method was used for all tokens for all subjects, even when the first and second formants were resolved by the LPC display. Totals of 240 measures per subject and 2,880 measurements for the 12 subjects were recorded.

Bandwidth for wide-band spectrograms was determined on a "gender-specific" basis using the narrowest appropriate bandwidth. The speech of the male speakers was analyzed with a bandwidth of 146 Hz; the speech of the female speakers with a bandwidth of 293 Hz.

Prosodic Contrasts

The acoustic measures were analyzed to provide information about the speech characteristics of subjects with cerebellar pathology and of normal subjects by assessing the effect of cerebellar pathology on the production of prosody as revealed by the control of duration and timing and the frequencies of F2, F1 and f0 in syllable production in four pairs of contrastive conditions; and 2) determining the relation between durational differences, spectral dynamics and f0 in each of the four contrasts. The four prosodic contrasts are:

(1) +pf+a vs. −pf+a: accented syllables in phrase-final (+pf+a) vs. non-phrase final (−pf+a) position;
(2) −pf+a vs. −pf−a: accented (−pf+a) vs. unaccented syllables (−pf−a) in non phrase-final positions;
(3) +n+a vs. −n−a: nuclear accented (+n+a) vs. post-nuclear unaccented (−n−a) syllables; and
(4) −n−a vs. red: post-nuclear unaccented (−n−a) vs. reduced (red) CVC syllables (i.e., full versus reduced vowels).

Statistical Design

The acoustic measures were analyzed according to a formula based on the 4 contrasts. A "D" score, known as the Euclidean Distance Metric,) provided an overall rating of speech deterioration for each of the cerebellar subjects. The "D" score was based on the differences among all four contrast values between each cerebellar speaker and the normal matched control.

D=(Cer: (+pf+a)−(−pf+a)−Nor: (+pf+a)−(−pf+a))2+(Cer: [−pf+a]−[−pf−a ]−Nor: (−pf+a)−(−pf−a))2+(Cer: (+n+a)−(−n−a)−Nor (+n+a)−(−n−a))2+(Cer: (−n−a)−(red)−Nor: (−n−a)−(red))2.

wherein Cer=cerebellar subject and Nor=normal subject.

Pearson rank-order correlations were used to determine the relation between cerebellar degeneration and speech deterioration.

The statistical analysis of the acoustic data was divided into two analyses of variance. The first analysis examined the three main effects: the effect of neurological status, the effect of prosodic condition, and the interaction between these two.

In the second analysis, the interaction was studied with pair-wise comparisons focused on mean differences of neurological status and then mean differences of prosodic conditions. Each of the four contrasts was examined for the four acoustic measures of syllable duration, F1, F2 and f0 frequencies at the mid-point of the phonated vowel segment.

The Effects of Prosodic Condition on Syllable Durations

Durations for the sequence "pap" produced by the twelve subjects across six different prosodic conditions were examined. Three main effects were examined for the measure of syllable duration: the effect of neurological condition, the effect of prosodic condition, and the interaction of these conditions (see Table 3). Main effects were found to be significant for all of the measures of syllable duration: the effect of neurological status: p=0.003<0.01<0.05; prosodic reconditions: p=0.001<0.001<0.05 and the interaction between neurological status and prosodic condition: p=0.001<0.001<0.05.

TABLE 3

| Source | Type III Sum of Squares | df | Mean Square | F | Sig. |
|---|---|---|---|---|---|
| Neurological status | 339926.082 | 1 | 339926.082 | 29.503 | p < .003** |
| Prosodic condition | 57609.006 | 5 | 11521.801 | 11.271 | p < .001*** |
| Interaction between neurological status & prosodic condition. | 122624.913 | 5 | 24524.983 | 6.795 | p < .001*** |

*The mean difference is significant at the .050 level; **significant at the .01 level.

The findings for each of the mean values of syllable duration for each of the six prosodic conditions when compared across neurological status were statistically significant. Moreover, the unaccented conditions, −pf−a, −n−a and the reduced syllable, showed significant differences between groups at the greater than 0.01 level. Table 4 presents the statistical analysis (marginal means and differences of syllable durations) of the interaction between prosodic condition and neurological status.

TABLE 4

| Prosodic Condition | Neurological Status | Mean | Mean Difference | Sig |
|---|---|---|---|---|
| +pf+a | Cerebellar | 637.531 | 273.831 | .015* |
|  | Normal | 363.700 |  |  |
| −pf+a | Cerebellar | 347.493 | 76.904 | .020* |
|  | Normal | 270.589 |  |  |
| −pf−a | Cerebellar | 321.561 | 80.448 | .013** |
|  | Normal | 241.113 |  |  |
| +n+a | Cerebellar | 334.817 | 71.600 | .019* |
|  | Normal | 263.217 |  |  |
| −n−a | Cerebellar | 329.341 | 90.424 | .005** |
|  | Normal | 238.917 |  |  |
| red | Cerebellar | 399.991 | 231.324 | .006** |
|  | Normal | 168.667 |  |  |

*The mean difference is significant at the .050 level;
**significant at the .01 level.

Table 5 presents the data for the Pair-wise comparisons (mean syllable duration differences between prosodic conditions) within each subject group: normal and cerebellar.

TABLE 5

| Neurological Status | Prosodic Contrast | Means | Mean Difference | Sig |
|---|---|---|---|---|
| Normal | +pf+a vs. −pf+a | 363.700–270.589 | 93.111* | .030* |
|  | −pf+a vs. −pf−a | 270.589–241.113 | 29.587* | .014* |
|  | +n+a vs. −n−a | 263.217–238.917 | 24.300** | .007** |
|  | −n−a vs. red | 238.917–168.667 | 70.250** | .004** |
| Cerebellar | +pf+a vs. −pf−a | 637.531–347.493 | 290.039* | .018* |
|  | −pf+a vs. −pf−a | 347.493–321.561 | 25.931 | .073 |
|  | +n+a vs. −n−a | 334.817–329.341 | 5.476 | .627 |
|  | −n−a vs. red | 329.341–399.991 | −70.650 | .344 |

*The mean difference is significant at the .05 level;
**significant at .01 level.

For the cerebellar group the difference between +pf+a and −pf+a conditions was significant while the remaining three contrasts were not. The normal group showed significant differences for all of the four prosodic contrasts: In short, prosodic contrasts showed significant differences between conditions for all four contrasts in the normal group. (FIG.

7) Examination of each group exclusive of the other group showed the greatest degree of lengthening across conditions for the phrase-final position. However, a comparison between groups showed that the duration of the reduced syllable for the ataxic speakers (400 ms) was longer than the phrase-final accented condition of the normal speakers (364 ms). Table 4 presents the mean values for each of the prosodic conditions for both groups.

Duration

Each of the prosodic conditions showed a significant difference between the normal and the cerebellar groups for the measure of syllable duration. The four contrasts, when examined within each group, showed one significantly different contrast (+pf+a vs. −pf+a) for the cerebellar group whereas the normal group showed significant differences for all of the four contrasts investigated. Between-group differences in the production of contrasts, were significant (+pf+a vs. −pf+a) and nearly significant for (−n−a vs. red). These two contrasts present evidence for different patterns in accented lengthening and syllable reduction across groups.

The results also statistically support the claim that ataxic speakers were not able to reduce syllables in the way that normal speakers did. All of the normal speakers showed a significant reduction in the duration of the reduced syllable ($p=0.004<0.01$: Table 5); the ataxic speakers did not show this reduction.

The Effects of Prosodic Condition on Formant Frequencies

The F2 and F1 mid-point frequencies were examined for the syllable "pap" produced by the twelve subjects across six different prosodic conditions. Table 6 and Table 9 present the results for the significance of three main effects for measures of F2 and F1 frequency: the effect of neurological condition, the effect of prosodic condition and the interaction of these conditions. The main effect of the interaction of the F2 measure was significant ($p=0.05$) (See Table 6).

TABLE 6

| Source | Type III Sum of Squares | df | Mean Square | F | Sig. |
|---|---|---|---|---|---|
| Neurological status | 5666.491 | 1 | 5666.491 | .263 | p = .630 |
| Prosodic condition | 75516.058 | 5 | 15123.212 | 1.535 | p = .215 |
| Interaction between neurological status & prosodic condition | 132727.328 | 1.298 | 102233.721 | 5.456 | p = .050* |

*The mean difference is significant at the .050 level.

For F1, two main effects were found to be significant: prosodic condition and the interaction of neurological status and prosodic condition (Table 9).

TABLE 9

| Source | Type III Sum of Squares | df | Mean Square | F | Sig. |
|---|---|---|---|---|---|
| Neurological status | 1776.466 | 1 | 1776.466 | .193 | p = .679 |
| Prosodic condition | 560260.076 | 5 | 112052.015 | 63.011 | p < .001*** |
| Interaction between neurological status & prosodic condition | 97985.795 | 5 | 19597.159 | 9.577 | p < .001*** |

***The mean difference is significant at the .001 level.

The Effects of Prosodic Condition on F2 Frequency

An examination of the data provided in Table 7 shows the main effect of neurological status on F2 mid-point frequency values averaged over the six prosodic conditions. The mean across conditions did not differ significantly between groups. The average value for the cerebellar subjects was 1202 Hz.; for the normal group, 1219 Hz. The values among conditions, however, varied significantly in both groups, thus the difference between means was not a true indication of the difference between the patterns revealed by closer analysis of the data.

The data in Table 7 also reflects the interaction between neurological status and prosodic conditions. Normal speakers showed a distinct pattern of differences across conditions. The lowest mean F2 frequency for the normal group occurred in the reduced condition (1074 Hz). In contrast, the highest mean F2 frequency was in the non-phrase-final accented condition −pf+a (1296 Hz). Normal speakers consistently produced higher mean F2 frequencies for the two conditions of −pf+a (1296 Hz). and +n+a (1289 Hz), while the −a conditions had relatively lower mean F2 frequencies (−pf−a: 1205 Hz. and −n−a: 1217 Hz). The mean F2 frequency (1235 Hz) in the +pf+a condition was lower than in the other +a conditions and close to the −a conditions.

TABLE 7

| Prosodic Condition | Neurological Status | Mean | Mean Difference | Sig |
|---|---|---|---|---|
| +pf+a | Cerebellar | 1225.133 | −10.083 | .855 |
| | Normal | 1235.217 | | |
| −pf+a | Cerebellar | 1207.104 | −88.472 | .168 |
| | Normal | 1295.576 | | |
| −pf−a | Cerebellar | 1193.250 | −11.669 | .803 |
| | Normal | 1204.919 | | |
| +n+a | Cerebellar | 1161.817 | −126.950 | .124 |
| | Normal | 1288.767 | | |
| −n−a | Cerebellar | 1200.404 | −16.513 | .582 |
| | Normal | 1216.917 | | |
| Red | Cerebellar | 1221.715 | 147.231* | .022* |
| | Normal | 1074.483 | | |

*The mean difference is significant at the .050 level.

Cerebellar ataxic speakers did not produce the range of F2 frequency differences seen in normals. F2 values for cerebellar speakers ranged from 1161 Hz. to 1225 Hz. (a 64 Hz. difference) whereas normal speakers ranged from 1074 Hz. to 1296 Hz. (a 222 Hz. difference). The two highest values for cerebellar speakers across the prosodic conditions were the red condition at 1222 Hz. and the +pf+a condition: 1225 Hz., while the +n+a was among the lower values. Therefore, the cerebellar speakers did not distinguish accented and unaccented conditions as did the normals. The only condition to show a significant difference between groups for the mean F2 frequency was the reduced condition: $p=0.022<0.05$.

Figure 8:
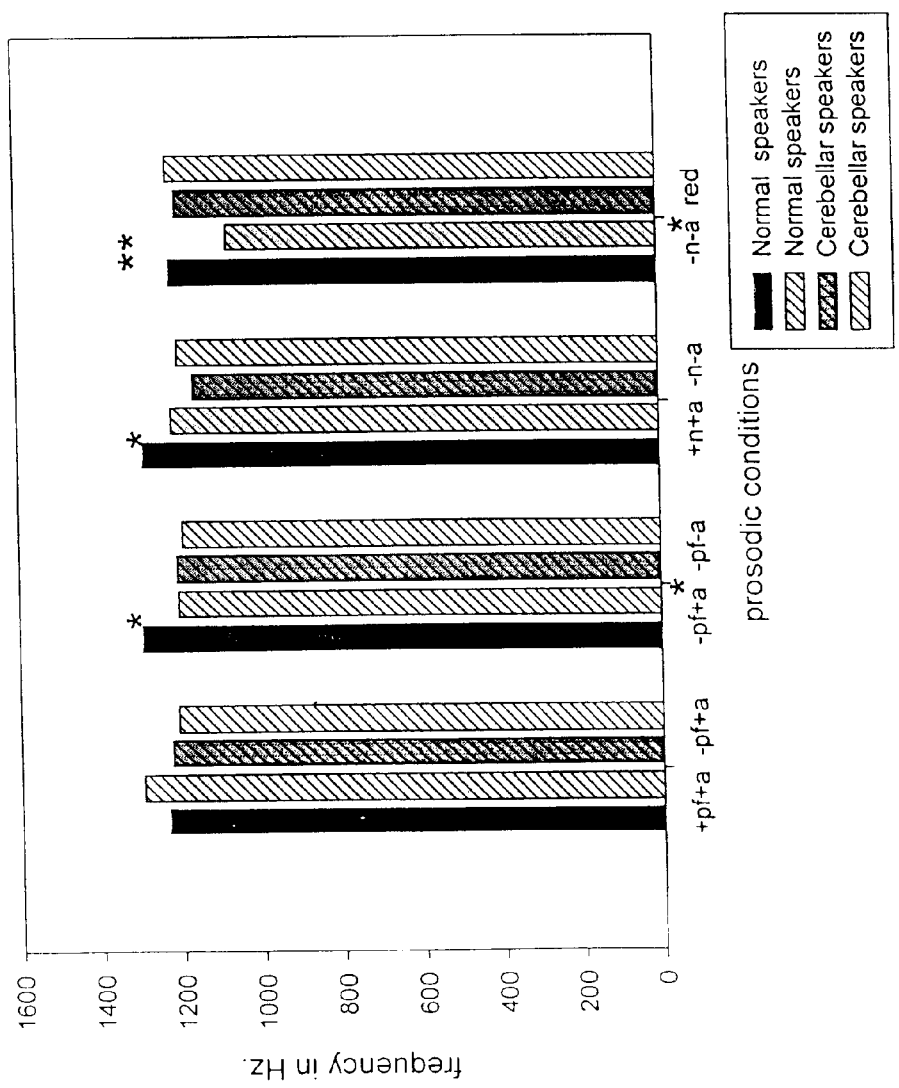
FIG. 8 shows mean F2 in Hz for each of the four prosodic contrasts for cerebellar ataxic speakers and normal speakers. The mean contrasts for each group are represented as significant by *($p<0.05$) and **($p<0.01$). The mean difference between groups for each of the four contrasts is marked for significance on the x-axis:−pf+a/−pf−a and −n−a/red.

The four contrasts between prosodic conditions were analyzed by pair-wise comparisons (mean mid-point F2 frequency differences between prosodic conditions) for each group: normal and cerebellar (Table 8 and FIG. 8).

TABLE 8

| Neurological Status | Prosodic Contrast | Means | Mean Difference | Sig.a |
|---|---|---|---|---|
| Normal | +pf+a vs. −pf+a | 1235.217–1295.576 | −60.359 | .271 |
| | −pf+a vs. | 1295.576–1204.919 | 90.656* | .039* |

TABLE 8-continued

| Neurological Status | Prosodic Contrast | Means | Mean Difference | Sig.a |
|---|---|---|---|---|
| | -pf-a | | | |
| | +n+a vs. -n-a | 1288.767-1216.917 | 71.850* | .018* |
| | -n-a vs. red | 1216.917-1074.483 | 142.433* | .006** |
| Cerebellar | +pf+a vs. -pf+a | 1225.133-1207.104 | 18.030 | .553 |

*The mean difference is significant at the .050 level;
**significance at .01 level.
a Adjustment for multiple comparisons: Least Significant Difference (equivalent to no adjustments.)

The cerebellar group showed no significant differences between the mean F2 frequencies for any of the four prosodic contrasts. In contrast, the normal group showed significant differences for three of the four prosodic contrasts: -pf+a vs. -pf-a (p=0.039<0.05); +n+a vs. -n-a (p=0.018<0.05) and -n-a vs. red (p=0.006<0.01). Although the +pf+a vs. -pf+a difference was not statistically significant, an examination of differences between groups suggests different dynamics of lengthening within that contrast (FIG. 8). The normal speakers, as a group, showed a relatively higher average F2 frequency for the accented syllable in non-final position as compared to the accented syllable in phrase-final position. Cerebellar speakers as a group did not show this pattern. While the normal speakers consistently lowered the F2 frequency for the -a conditions relative to the +a conditions in the comparisons of -pf+a vs. -pf-a, +n+a vs. -n-a and -n-a vs. red, the cerebellar speakers did not.

The Effects of Prosodic Condition on F1 Frequency

The effects of neurological status, prosodic condition, and the interaction between neurological status and prosodic condition for the acoustic measure of F1 frequency are shown in Table 9. The main effects of prosodic condition (p=0.000<0.001) and of the interaction between prosodic conditions and neurological status (p=0.000<0.001) were significant.

The main effect of neurological status on F1 mid-point frequency across the six prosodic conditions is shown in Table 10. The means across conditions for the vowel "a" in the syllable "pap" did not differ significantly between groups (Cerebellar: 774 Hz and Normal: 784 Hz).

The interaction between neurological status and prosodic conditions is also shown in Table 10. As with F2 frequency, there were differences in the F1 means between groups for each of the prosodic conditions. For normal speakers the lowest mean F1 frequency was in the red (518 Hz.). In contrast, the highest mean value was in the -pf+a condition (866 Hz.). Normal speakers consistently produced higher frequency values for the two accented conditions of -pf+a (866 Hz.) and +n+a (864 Hz.), while the unaccented conditions had relatively lower mean F1 frequencies (-pf-a 808 Hz. and -n-a, 795 Hz.). One accented condition, +pf+a (853 Hz.) was lower than the other two phrase and accent positions (-pf+a and +n+a).

TABLE 10

| Prosodic Condition | Neurological Status | Mean | Mean Difference | Sig.a |
|---|---|---|---|---|
| +pf+a | Cerebellar | 847.917 | -4.833 | .879 |
| | Normal | 852.750 | | |

TABLE 10-continued

| Prosodic Condition | Neurological Status | Mean | Mean Difference | Sig.a |
|---|---|---|---|---|
| -pf+a | Cerebellar | 779.922 | -86.572 | .063 |
| | Normal | 866.494 | | |
| -pf-a | Cerebellar | 774.980 | -33.364 | .292 |
| | Normal | 808.344 | | |
| +n+a | Cerebellar | 789.220 | -74.613 | .140 |
| | Normal | 863.833 | | |
| -n-a | Cerebellar | 796.761 | 1.744 | .961 |
| | Normal | 795.017 | | |
| red | Cerebellar | 655.815 | 138.031 | .001*** |
| | Normal | 517.783 | | |

***The mean difference is significant at the .001 level.

The range of mean F1 frequencies for cerebellar ataxic speakers was 192 Hz (848 Hz–656 Hz), which was smaller than that for the normal speakers which was 358 Hz (866–578 Hz). The two highest mean F1 frequencies for cerebellar speakers were -n-a (797 Hz.) and +pf+a (848 Hz.). As with F2 frequency, the cerebellar speakers did not show a pattern of F1 frequencies that distinguish accented (+a) from unaccented (-a) as did the normal subjects. Only the red condition showed a significant difference between groups for F1 frequency (p=0.001<0.001) (Table 10).

Figure 9:
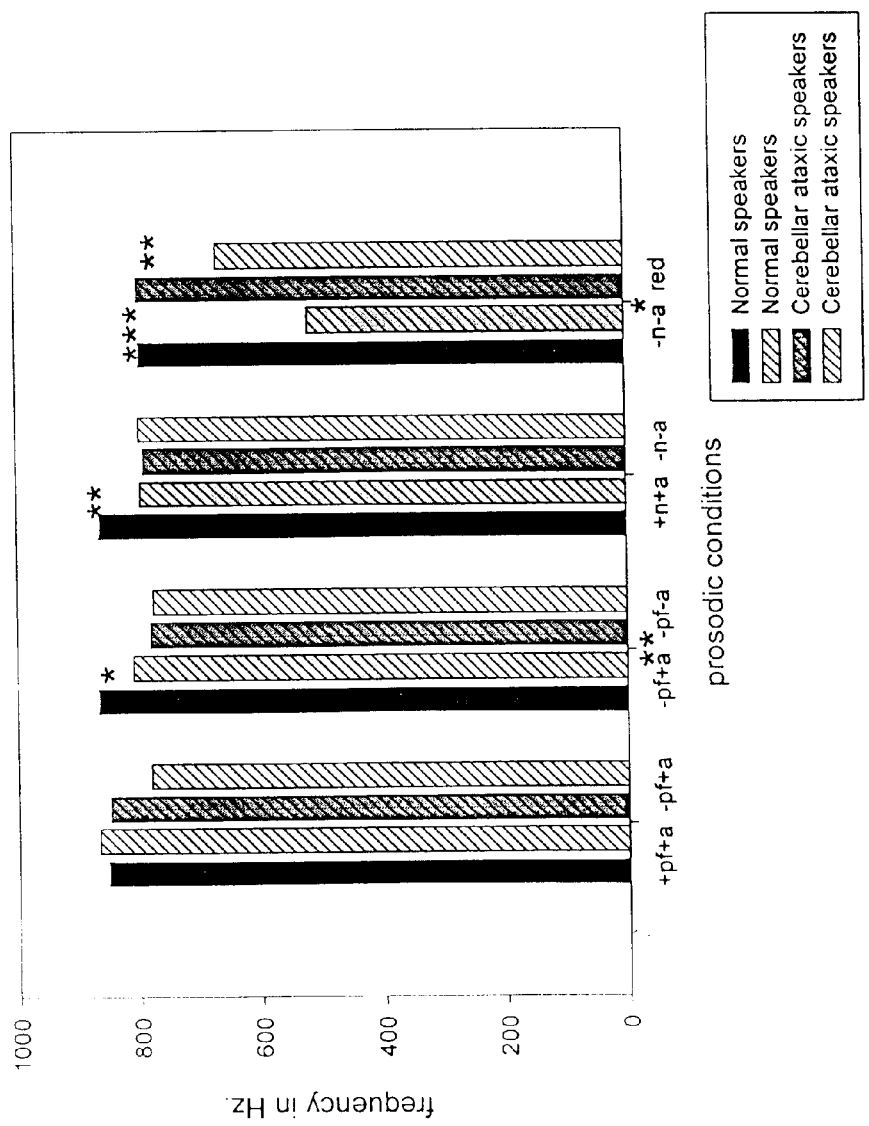
FIG. 9 shows mean F1 frequencies at mid-point in Hz for each of the four prosodic contrasts for cerebellar ataxic speakers and normal speakers. The differences in means within each group is represented as significant by *(p<0.05) and (p<0.01) and *(p<0.001). The mean difference between groups for each of the four contrasts is marked for significance on the x axis–pf+a/–pf–a and –n–a/red.

The four contrasts between prosodic conditions were analyzed within each subject group data shown in Table 11. The cerebellar group showed a significant difference for mean F1 frequencies only in the -n-a vs. red contrast (p=0.01<0.01). The normal group however, showed significant differences for three of the four prosodic contrasts: -pf+a vs. -pf+a (p=0.025<0.05) +n+a vs. -n-a (p=0.01=0.01) and -n-a vs. red (p=0.000<0.001) (FIG. 9).

TABLE 11

| Neurological Status | Prosodic Contrast | Means | Mean Difference | Sig.a |
|---|---|---|---|---|
| Normal | +pf+a vs. -pf+a | 852.750-866.494 | -13.744 | .634 |
| | -pf+a vs. -pf-a | 866.494-808.344 | 58.151* | .025* |
| | +n+a vs. -n-a | 863.833-795.017 | 68.817* | .010** |
| | -n-a vs. red | 795.017-517.783 | 277.233* | .000*** |
| Cerebellar | +pf+a vs. -pf+a | 847.917-779.922 | 67.994 | .064 |
| | -pf+a vs. -pf-a | 779.922-774.980 | 4.943 | .616 |
| | +n+a vs. -n-a | 789.220-796.761 | -7.541 | .834 |
| | -n-a vs. red | 796.761-655.815 | 140.946* | .010** |

*The mean difference is significant at the .050 level,
**p = .01,
***p < .001.

While the normal speakers consistently lowered the F1 frequency for the unaccented (-a) conditions relative to the +a conditions in the -pf+a vs. -pf-a, +n+a vs. -n-a and -n-a vs. red contrasts, the cerebellar speakers did not follow this pattern. Indeed, three of the six cerebellar speakers all increased the -a condition in the +n+a vs. -n-a contrast.

The Effects of Prosodic Condition on Fundamental Frequency f0

Table 12 presents the data for the three main effects of neurological status, prosodic condition and the interaction between neurological status and prosodic condition for fundamental frequency. Two of the three main effects were found to be significant: the effect of prosodic condition (p=0.000<0.001) and the interaction between neurological status and prosodic condition (p=0.000<0.001).

TABLE 12

| Source | Type III Sum of Squares | Df | Mean Square | F | Sig. |
|---|---|---|---|---|---|
| Neurological status | 210.647 | 1 | 210.647 | .090 | p = .777 |
| Prosodic condition | 23674.229 | 5 | 4734.846 | 16.750 | p < .001*** |
| Interaction between neurological status and prosodic condition | 12547.678 | 5 | 2509.536 | 6.632 | p < .001*** |

***The mean difference is significant at the .001 level.

Table 13 presents the statistical analysis of the interaction between prosodic condition and neurological status. A significant difference between groups was found for the red condition (p=0.041<0.05). In addition, an examination of the means for each of the prosodic conditions revealed a tendency for differences between groups. As found in the measures of F2 and F1 frequency, normal speakers showed a distinct pattern of differences across conditions (FIG. 10), with the lowest mean f0 for the normal group occurring in the red condition with speakers averaging 130.8 Hz. In contrast, the highest value was +n+a condition at 212.5 Hz. Normal speakers produced higher frequency values for the accented (+a) conditions (−pf+a: 203.3 Hz. and +n+a 212.5 Hz.), while the unaccented (−a) conditions (−pf−a: 198.1 Hz., −n−a: 143.1 Hz.) were relatively lower in frequency. However, the +pf+a condition (190.8 Hz.) was lower than even the −pf−a (198.1 Hz.)

TABLE 13

| Prosodic Condition | Neurological Status | Mean | Mean Difference | Sig.a |
|---|---|---|---|---|
| +pf+a | Cerebellar | 176.617 | −18.133 | .253 |
|  | Normal | 190.750 |  |  |
| −pf+a | Cerebellar | 181.302 | −21.957 | .165 |
|  | Normal | 203.259 |  |  |
| −pf−a | Cerebellar | 184.528 | −13.607 | .504 |
|  | Normal | 198.135 |  |  |
| +n+a | Cerebellar | 180.344 | −32.172 | .067 |
|  | Normal | 212.517 |  |  |
| −n−a | Cerebellar | 169.172 | 26.089 | .181 |
|  | Normal | 143.083 |  |  |
| red | Cerebellar | 170.068 | 39.256* | .041* |
|  | Normal | 130.812 |  |  |

*The mean difference is significant at the .050 level.

Figure 10:
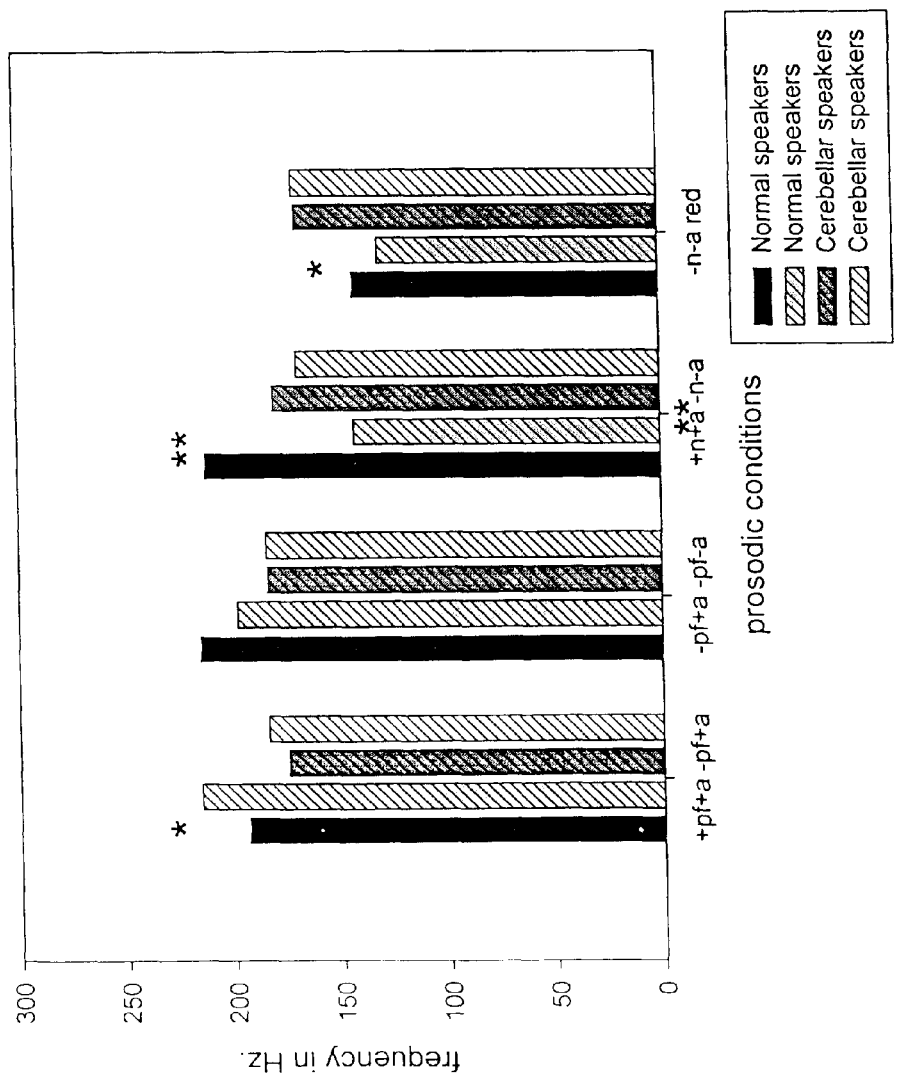
Figure 11:
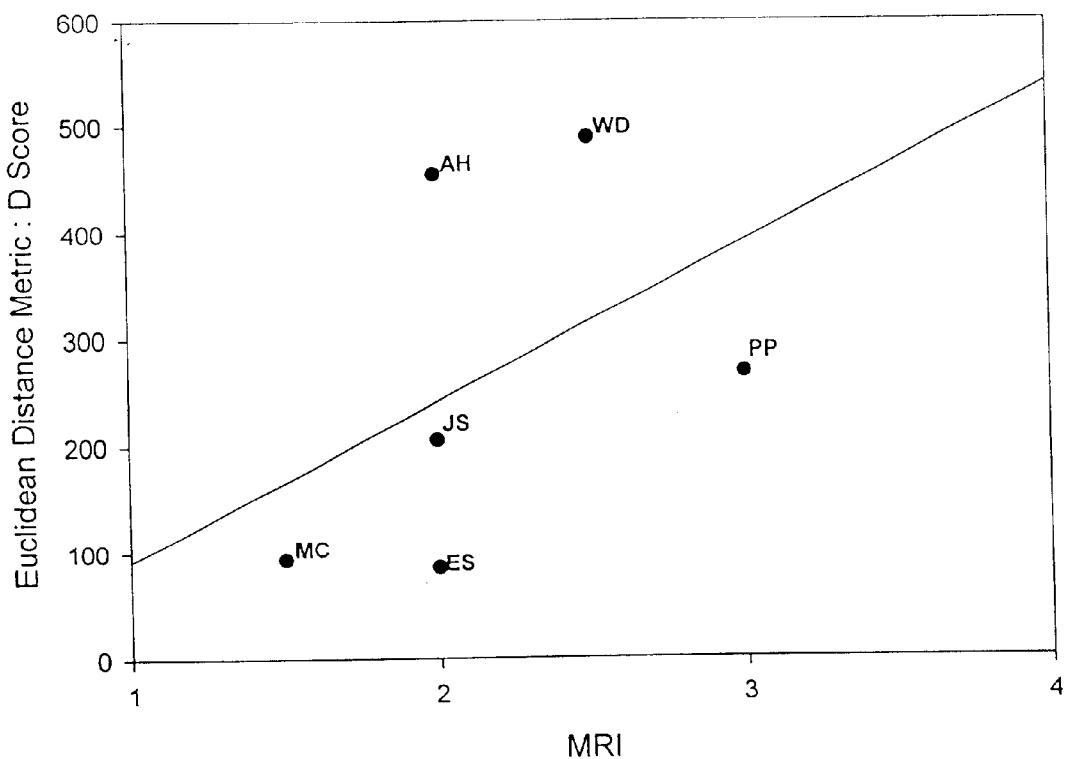
FIG. 11 shows the Pearson Correlation (r=0.440) between the average MRI rating for cerebellar involvement versus the D statistic as a measure of speech deterioration for each of the six cerebellar ataxic speakers for the measure of the syllable duration.

The cerebellar speakers did not produce the range of f0 differences seen in normals: (FIG. 10). Cerebellar speakers' f0 values ranged from 169 Hz. to 185 Hz. (16 Hz. difference) whereas normal speakers' f0 values ranged from 131 Hz. to 213 Hz. (82 Hz. difference) across prosodic conditions. The highest f0 for cerebellar ataxic speakers was the +pf−a condition (185 Hz.) and the lowest value was for the −n−a condition at (169 Hz.). The only condition to show a significant difference between groups for the measure of f0 was the +n+a vs. −n−a condition (p=0.009<0.01). The four contrasts between prosodic conditions were analyzed for each subject group (Table 14 and FIG. 10). The cerebellar group showed no significant differences in the mean f0 for any of the four prosodic contrasts. In contrast, the normal group showed significant differences for three of the four prosodic contrasts: +pf+a vs. −pf+a (p=0.036<0.05*); +n+a vs. −n−a (p=0.002<0.01**) and −n−a vs. red (p=0.045<0.05*). The one contrast that was not significant for the normal group in the measure of f0 was the −p f+a vs. −pf−a.

TABLE 14

| Neurological Status | Prosodic Contrast | Means | Mean Difference | Sig. |
|---|---|---|---|---|
| Normal | +pf+a vs. −pf+a | 190.750–203.259 | −12.509 | .036* |
|  | −pf+a vs. −pf−a | 203.259–198.135 | 5.125 | .434 |
|  | +n+a vs. −n−a | 212.517–143.083 | 69.433** | .002** |
|  | −n−a vs. red | 143.083–130.812 | 12.271* | .045* |
| Cerebellar | +pf+a vs. −pf+a | 176.617–181.302 | −8.685 | .068 |
|  | −pf+a vs. −pf−a | 181.302–184.528 | −3.226 | .545 |
|  | +n+a vs. −n−a | 180.344–169.172 | 10.277 | .552 |
|  | −n−a vs. red | 169.172–170.068 | −.895 | .926 |

*The mean difference is significant at the .050 level;
** at the .01 level.

Across the four acoustic measures investigated, significant differences for syllable durations, formant measures and for fundamental frequency measures occur more often (Normals: 13/16:81.25%; Cerebellar: 2/16:12.5) in normal speakers' data than in those speakers with cerebellar pathology. The normal speakers showed significant differences for final lengthening (+pf+a vs. −pf+a) in the measure of f0 but not in the formant frequencies. The F1 and F2 frequencies showed significant differences for +a in the contrast −pf+a vs. −pf−a, while the f0 difference was not significant for this contrast (Tables 5, 8, 11 and 14).

Conclusions

The effects of Cerebellar Degeneration on f0

Of the six prosodic conditions investigated, the only condition to show a significant difference between the normal and cerebellar groups was the reduced syllable: red (Table 13). While normal speakers produced significant differences (Table 14) between conditions for three of the four contrasts analyzed (+pf+a vs. −pf+a, +n+a vs. −n−a and −n−a vs. red), the cerebellar speakers did not produce significant differences for any of the four contrasts. The range of f0 (Table 13) for the normal speakers (82 Hz) was clearly greater than that for the cerebellar speakers (16 Hz). In addition, the cerebellar speakers produced the highest mean f0 in an unaccented condition: −pf−a (185 Hz). While the normal speakers produced a systematic pattern for prosodically distinct syllables (FIG. 10), the cerebellar group did not.

Perhaps the most significant finding for the measure of f0 was the difference found in normal speakers (FIG. 10, Table 14) for the contrast +pf+a vs. −pf+a. The normal speakers produced a significant difference in this contrast with the f0 lower in the +pf+a than in the −pf+a condition. Although there was no significant difference between conditions for the cerebellar speakers for the contrast +pf+a vs. −pf+a (Table 14), the pattern for the production of this contrast for cerebellar speakers was similar to that of the normal speakers in that the cerebellar speakers as a group show a lower f0 for the +pf condition (FIG. 10). The individual data show that four of the six cerebellar speakers use a lower the f0 in +pf for the contrast +pf+a vs. −pf+a while two speakers showed little difference in f0 between these conditions.

Correlations Between Cerebellar Degeneration and Speech Disturbance

The D scores, MRI ratings and Pearson-correlations between these measures for each of the six cerebellar ataxic speakers is shown in Table 16. FIGS. 11 through 14 graphically illustrate these correlations.

TABLE 16

| Subject | Cerebellar syndrome | MRI Ratings | Euclidean Distance Metric: D scores | | | |
|---|---|---|---|---|---|---|
| | | | Duration | F2 | F1 | f0 |
| 1 | Pure recessive | 2.0 | 454.69 | 132.72 | 188.05 | 90.54 |
| 2 | unknown | 3.0 | 267.90 | 177.59 | 91.32 | 87.85 |
| 3 | OPCA | 2.5 | 487.81 | 162.60 | 176.10 | 54.60 |
| 4 | Friedreich's | 2.0 | 205.52 | 621.52 | 373.98 | 102.40 |
| 5 | Friedreich's | 2.0 | 85.62 | 274.48 | 296.67 | 58.45 |
| 6 | Friedreich's | 1.5 | 98.38 | 245.78 | 228.81 | 23.50 |
| | Pearson correlation | | r = .440 | r = −.285 | r = −.630 | r = .446 |

Correlations Between Measures of Syllable Duration and Cerebellar Degeneration

A moderate positive correlation (r=0.444) between speech disturbance and cerebellar degeneration was found for the measure of syllable duration. An examination of the data (Table 16 and FIG. 11) showed that the three subjects with the more severe speech deterioration had cerebellar degeneration of etiology other than Friedreich's ataxia. The subjects 3 (D=488), 1 (D=455) and 2 (D=268) had more deterioration as measured in syllable duration than the three subjects with Friedreich's ataxia 4 (D=206), 5 (D=86) and 6 (D=98). Thus, the pattern among the cerebellar subjects differed depending on the relative involvement of the cerebellum and the etiology of cerebellar degeneration.

Correlations Between Measures of F2 and Cerebellar Degeneration

Figure 12:
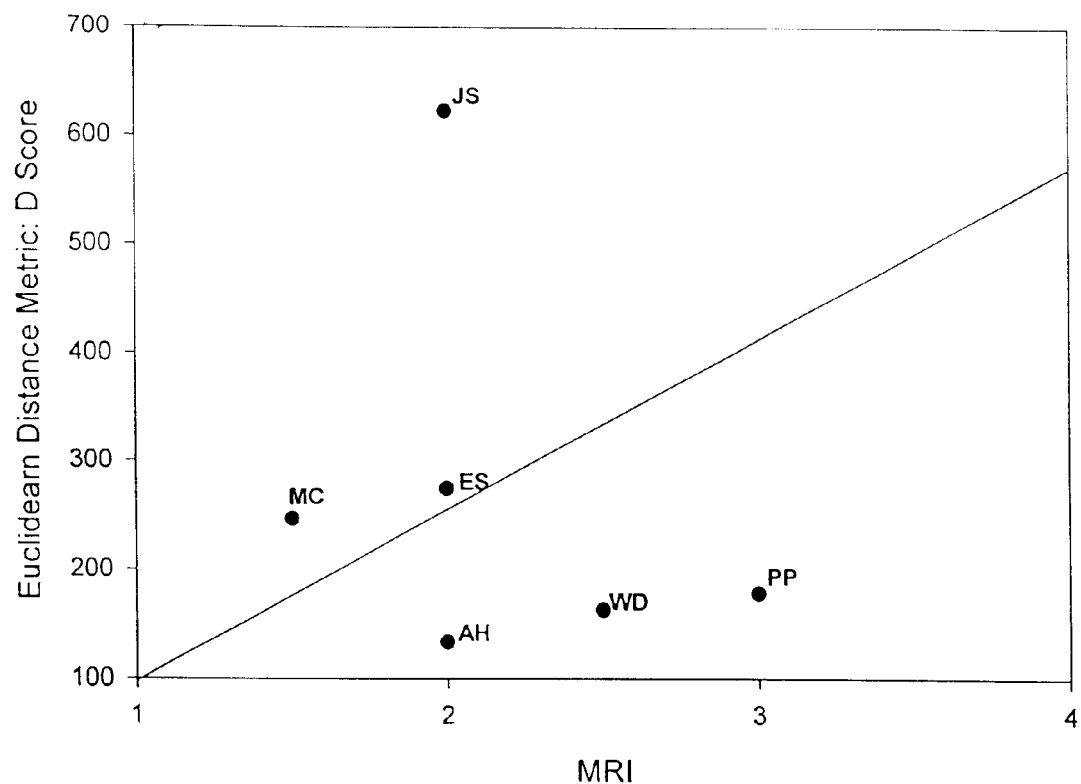
FIG. 12 shows the Pearson Correlation (r=0.285) between the average MRI rating for cerebellar involvement versus the D statistic as a measure of speech deterioration for each of the six cerebellar ataxic speakers for the of F2.
Figure 13:
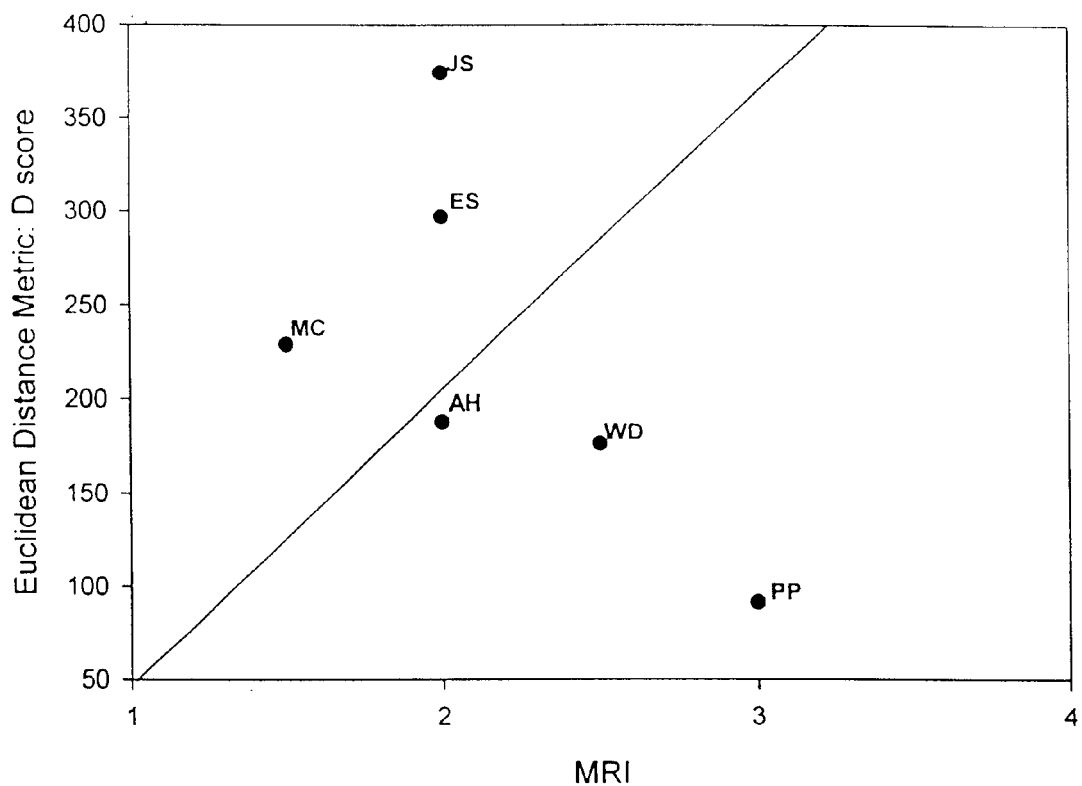
FIG. 13 shows the Pearson Correlation (r=0.630) between the average MRI rating for cerebellar involvement versus the D statistic as a measure of speech deterioration for each of the six cerebellar ataxic speakers for the measure F1.
Figure 14:
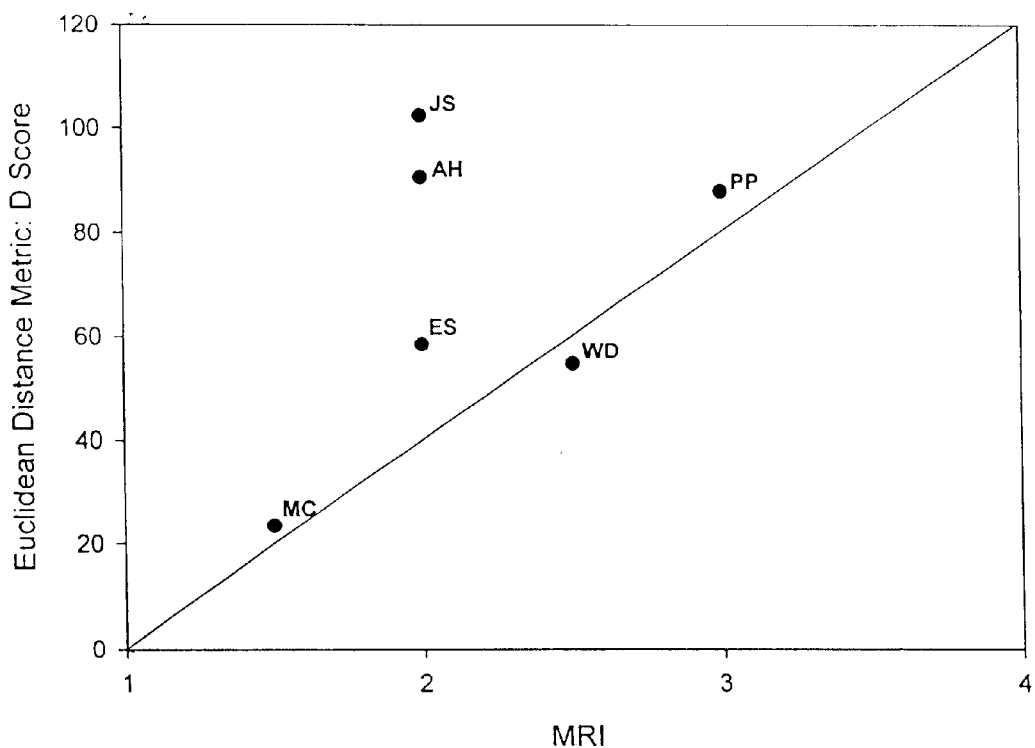
FIG. 14 show the Pearson Correlation (r=0.446) between the average MRI rating for cerebellar involvement versus the D statistic as a measure of speech deterioration for each of the six cerebellar ataxic speakers for the measure of $f_0$.
Figure 15:
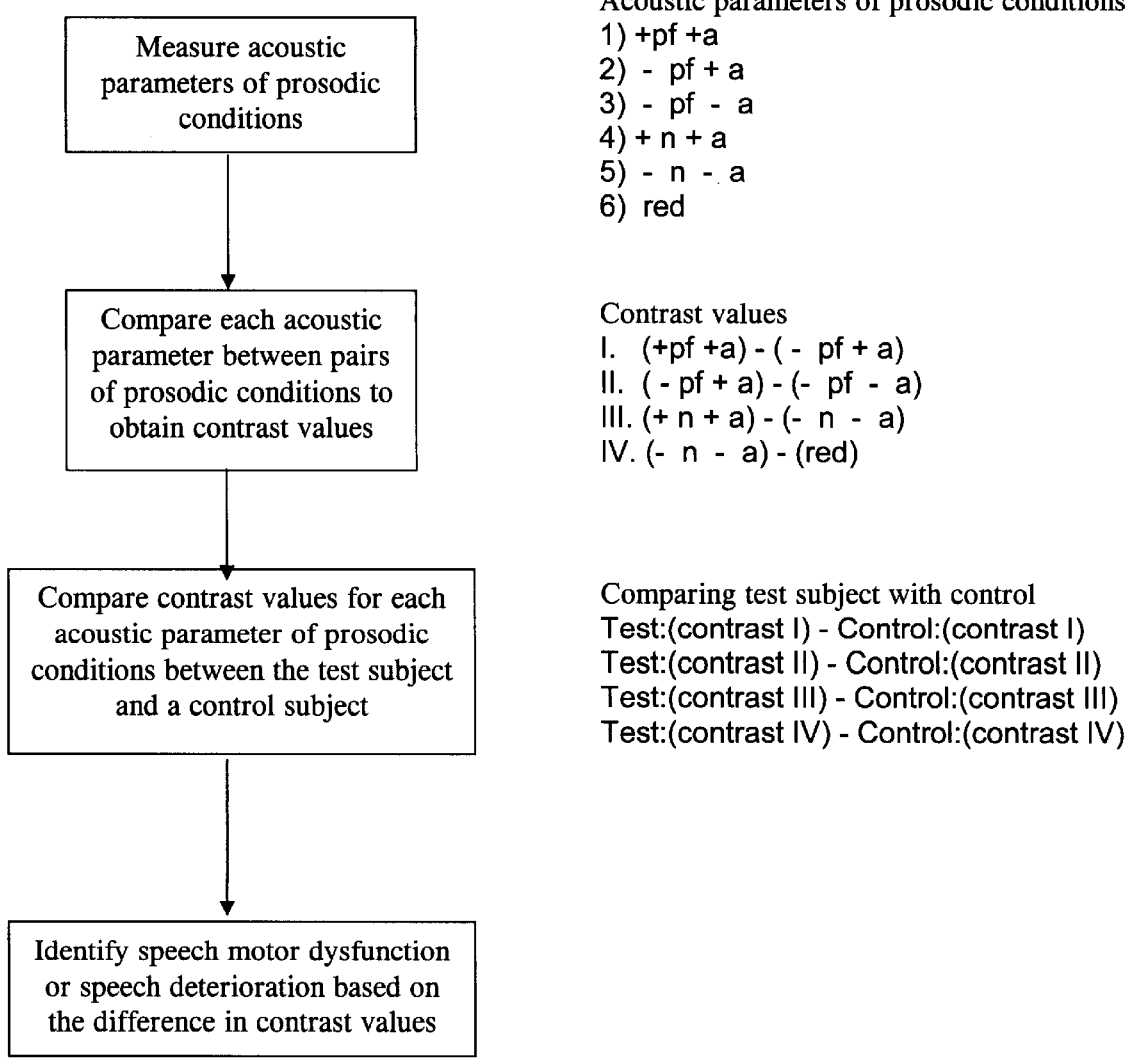
FIG. 15 shows a flow chart of the method of identifying speech motor dysfunction in accordance with the preferred embodiment of the invention.

A mild negative correlation (r=0.285) for the measure of F2 was found between speech disturbance and cerebellar degeneration (see FIG. 12). Three of the six cerebellar subjects with Friedreich's ataxia showed more deterioration in the measure of F2 than the three subjects with cerebellar degeneration of other etiologies.

Correlation Between Measures of F1 and Cerebellar Cegeneration

There was a strong negative correlation for the measure of F1 frequency (r=0.630) between speech disturbance and cerebellar degeneration. The data is shown in Table 16 and FIG. 13. As with F2, but to a greater degree, the three subjects with Friedreich's ataxia, showed greater speech deterioration in the measure of F1 than the three subjects with cerebellar degenerations of other etiologies.

Correlation Between measures of f0 and Cerebellar Degeneration

There was a moderate positive correlation (r=0.446) for the measure of f0, between speech disturbance and cerebellar degeneration. The data is shown in Table 16 and FIG. 14. The three subjects with cerebellar degeneration of etiology other than Friedreich's showed more speech deterioration for the measure of f0 than the Friedreich's ataxic subjects.

Of the four acoustic measures investigated, syllable duration and fundamental frequency showed moderate positive correlations between speech disturbance and cerebellar degeneration using the D score. F1 showed a strong negative correlation and F2 a mild negative correlation between cerebellar degeneration and speech disturbance.

What is claimed is:

1. A method of identifying speech motor dysfunction in a test subject comprising:
   measuring one or more acoustic parameters of one or more prosodic conditions;
   comparing each acoustic parameter between pairs of prosodic conditions to obtain a contrast value; and
   comparing the contrast values for each acoustic parameter to contrast values of a normal subject,
   wherein a difference in contrast values between the test subject and the normal subject is correlated to speech motor dysfunction; and
   wherein the contrast values are compared using the equation $$(\text{Test: } (+pf+a)-(-pf+a)-\text{Control: } (+pf+a)-(-pf+a))^2 +$$
   $$(\text{Test: } (-pf+a)-(-pf-a)-\text{Control: } (-pf+a)-(-pf-a))^2 +$$
   $$(\text{Test: } (+n+a)-(-n-a)-\text{Control: } (+n+a)-(-n-a))^2 +$$
   $$(\text{Test: } (-n-a)-(\text{red})-\text{Control: } (-n-a)-(\text{red}))^2$$

wherein

| | |
   |---|---|
   | +pf+a = | accented syllables in phrase final; |
   | −pf+a = | accented syllables in non-phrase final; |
   | −pf−a = | unaccented syllables in non phrase final; |
   | +n+a = | nuclear accented; |
   | −n−a = | post-nuclear unaccented syllables; and |
   | red = | reduced CVC syllables. |
   | Test = | subject |
   | Control = | control. |

2. The method of claim 1 wherein the acoustic parameters are syllable duration, f0, F1 and F2.

3. The method of claim 1 wherein the prosodic conditions are (1) phrase-final accented (+pf+a), (2) non-phrase-final accented (−pf+a), (3) non-phrase-final unaccented (−pf−a), (4) nuclear accented (+n+a), (5) post nuclear unaccented (−n−a) and (6) reduced vowel (red).

4. The method of claim 1 wherein the subject is suffering from cerebellar degeneration.

5. A method of identifying speech deterioration in a test subject comprising
   measuring one or more acoustic parameters of one or more prosodic conditions;
   comparing each acoustic parameter between pairs of prosodic conditions to obtain a contrast value; and
   comparing the contrast values for each acoustic parameter to contrast values of a normal subject,
   wherein a difference in contrast values between the test subject and the normal subject is correlated to speech deterioration; and
   wherein the contrast values are compared using the equation; and $$(\text{Test: } (+pf+a)-(-pf+a)-\text{Control: } (+pf+a)-(-pf+a))^2 +$$
   $$(\text{Test: } (-pf+a)-(-pf-a)-\text{Control: } (-pf+a)-(-pf-a))^2 +$$
   $$(\text{Test: } (+n+a)-(-n-a)-\text{Control: } (+n+a)-(-n-a))^2 +$$
   $$(\text{Test: } (-n-a)-(\text{red})-\text{Control: } (-n-a)-(\text{red}))^2$$

wherein

| | |
|---|---|
| +pf+a = | accented syllables in phrase final; |
| –pf+a = | accented syllables in non-phrase final; |
| –pf–a = | unaccented syllables in non phrase final; |
| +n+a = | nuclear accented; |
| –n–a = | post-nuclear unaccented syllables; and |
| red = | reduced CVC syllables. |
| Test = | subject |
| Control = | control. |

6. The method of claim 5 wherein the subject is suffering from cerebellar degeneration.

7. The method of claim 5 wherein the acoustic parameters are syllable duration, f0, F1 and F2.

8. The method of claim 5 wherein the prosodic conditions are (1) phrase-final accented (+pf+a), (2) non-phrase-final accented (–pf+a), (3) non-phrase-final unaccented (–pf–a), (4) nuclear accented (+n+a), (5) post nuclear unaccented (–n–a) and (6) reduced vowel (red).

9. A method of diagnosing speech motor dysfunction in a test subject comprising measuring one or more acoustic parameters of one or more prosodic conditions;

comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to speech motor dysfunction; and wherein the contrast values are compared using the equation $$(\text{Test: }(+pf+a)-(-pf+a)-\text{Control: }(+pf+a)-(-pf+a))^2+$$

$$(\text{Test: }(-pf+a)-(-pf-a)-\text{Control: }(-pf+a)-(-pf-a))^2+$$

$$(\text{Test: }(+n+a)-(-n-a)-\text{Control: }(+n+a)-(-n-a))^2+$$

$$(\text{Test: }(-n-a)-(red)-\text{Control: }(-n-a)-(red))^2$$

wherein

| | |
|---|---|
| +pf+a = | accented syllables in phrase final; |
| –pf+a = | accented syllables in non-phrase final; |
| –pf–a = | unaccented syllables in non phrase final; |
| +n+a = | nuclear accented; |
| –n–a = | post-nuclear unaccented syllables; and |
| red = | reduced CVC syllables. |
| Test = | subject |
| Control = | control. |

10. The method of claim 9 wherein the acoustic parameters are syllable duration, f0, F1 and F2.

11. The method of claim 9 wherein the prosodic conditions are (1) phrase-final accented (+pf+a), (2) non-phrase-final accented (–pf+a), (3) non-phrase-final unaccented (–pf–a), (4) nuclear accented (+n+a), (5) post nuclear unaccented (–n–a) and (6) reduced vowel (red).

12. The method of claim 9 wherein the subject is suffering from cerebellar degeneration.

13. A method of rating the severity of speech motor dysfunction in a test subject comprising measuring one or more acoustic parameters of one or more prosodic conditions;

comparing each acoustic parameter between pairs of prosodic conditions to obtain a contrast value; and comparing the contrast values for each acoustic parameter to contrast values of a normal subject, wherein a difference in contrast values between the test subject and the normal subject is correlated to the severity of speech motor dysfunction; and wherein the contrast values are compared using the equation $$(\text{Test: }(+pf+a)-(-pf+a)-\text{Control: }(+pf+a)-(-pf+a))^2+$$

$$(\text{Test: }(-pf+a)-(-pf-a)-\text{Control: }(-pf+a)-(-pf-a))^2+$$

$$(\text{Test: }(+n+a)-(-n-a)-\text{Control: }(+n+a)-(-n-a))^2+$$

$$(\text{Test: }(-n-a)-(red)-\text{Control: }(-n-a)-(red))^2$$

wherein

| | |
|---|---|
| +pf+a = | accented syllables in phrase final; |
| –pf+a = | accented syllables in non-phrase final; |
| –pf–a = | unaccented syllables in non phrase final; |
| +n+a = | nuclear accented; |
| –n–a = | post-nuclear unaccented syllables; and |
| red = | reduced CVC syllables. |
| Test = | subject |
| Control = | control. |

14. The method of claim 13 wherein the acoustic parameters are syllable duration, f0, F1 and F2.

15. The method of claim 13 wherein the prosodic conditions are (1) phrase-final accented (+pf+a), (2) non-phrase-final accented (–pf+a), (3) non-phrase-final unaccented (–pf–a), (4) nuclear accented (+n+a), (5) post nuclear unaccented (–n–a) and (6) reduced vowel (red).

16. The method of claim 13 wherein the subject is suffering from cerebellar degeneration.

\* \* \* \* \*